United States Patent
Yang et al.

(10) Patent No.: US 12,409,158 B2
(45) Date of Patent: Sep. 9, 2025

(54) COMBINATION THERAPY FOR TREATING CANCER

(71) Applicant: GONGWIN BIOPHARM CO., LTD, Taipei (TW)

(72) Inventors: Chuan-Ching Yang, Taipei (TW); Shun-Chi Wu, Taipei (TW); Shu-Ying Cheng, Taipei (TW); Mao-Yuan Lin, Taipei (TW); Geng-Ruei Chang, Taipei (TW)

(73) Assignee: GONGWIN BIOPHARM CO., LTD, Taipei (TW)

( * ) Notice: Subject to any disclaimer, the term of this patent is extended or adjusted under 35 U.S.C. 154(b) by 0 days.

(21) Appl. No.: 18/186,816

(22) Filed: Mar. 20, 2023

(65) Prior Publication Data

US 2023/0321016 A1 Oct. 12, 2023

Related U.S. Application Data

(60) Provisional application No. 63/321,185, filed on Mar. 18, 2022.

(51) Int. Cl.
| | | |
|---|---|---|
| *A61K 31/18* | (2006.01) | |
| *A61K 31/519* | (2006.01) | |
| *A61K 31/7068* | (2006.01) | |
| *A61K 33/243* | (2019.01) | |
| *A61P 35/00* | (2006.01) | |

(52) U.S. Cl.
CPC .......... *A61K 31/18* (2013.01); *A61K 31/519* (2013.01); *A61K 31/7068* (2013.01); *A61K 33/243* (2019.01); *A61P 35/00* (2018.01)

(58) Field of Classification Search
CPC .... A61K 31/18; A61K 33/243; A61K 31/519; A61P 35/00
See application file for complete search history.

(56) References Cited

U.S. PATENT DOCUMENTS

| | | | |
|---|---|---|---|
| 9,668,990 B1 * | 6/2017 | Yang | ............... A61P 35/00 |
| 2011/0178046 A1 | 7/2011 | Ross et al. | |
| 2017/0128578 A1 | 5/2017 | Chen et al. | |

FOREIGN PATENT DOCUMENTS

| | | |
|---|---|---|
| WO | 2011009059 A2 | 1/2011 |
| WO | 2018118792 A1 | 6/2018 |

OTHER PUBLICATIONS

Barre-Sinoussi, F.; Montagutelli, X. "Animal models are essential to biological research: issues and perspectives" Future Sci OA. Nov. 2015; 1(4): FSO63. (Year: 2015).*

Gemcitabine (Gemcitabine Injection) [Highlights of Prescribing Information]. Durham, NC: Accord Healthcare, Inc.; Jul. 2018 (Year: 2018).*

(Continued)

*Primary Examiner* — Andrew D Kosar
*Assistant Examiner* — John D Mcanany
(74) *Attorney, Agent, or Firm* — HSML P.C.

(57) ABSTRACT

A method for treating proliferative diseases such as cancer in a subject by a combination therapy, which includes administering to the subject a pharmaceutical composition including a benzenesulfonamide derivative such as p-Toluenesulfonamide and at least one other therapeutic agents in a different classification of anticancer agents.

21 Claims, 25 Drawing Sheets
(6 of 25 Drawing Sheet(s) Filed in Color)
Specification includes a Sequence Listing.

(56) References Cited

OTHER PUBLICATIONS

Scagliotti, G.V.; Felip, E.; Besse, B.; et al. "An Open-Label, Multicenter, Randomized, Phase II Study of Pazopanib in Combination with Pemetrexed in First-Line Treatment of Patients with Advanced-Stage Non-Small-Cell Lung Cancer" Journal of Thoracic Oncology • vol. 8, No. 12, Dec. 2013 (Year: 2013).*
International Search Report and Written Opinion issued in PCT/US2023/064721, dated Jul. 17, 2023, 13 pages provided.
He et al., "Gemcitabine plus cisplatin chemotherapy with concurrent para-toluenesulfonamide local injection therapy for peripherally advanced nonsmall cell lung cancer larger than 3 cm in the greatest dimension", Anti-cancer drugs, 2009, vol. 20, pp. 838-844.

* cited by examiner

SEQUENCE LISTING

```
Sequence total quantity: 6
SEQ ID NO: 1              moltype = DNA   length = 20
FEATURE                   Location/Qualifiers
source                    1..20
                          mol_type = other DNA
                          organism = synthetic construct
SEQUENCE: 1
atggcttcta tgaggctgag                                                    20

SEQ ID NO: 2              moltype = DNA   length = 20
FEATURE                   Location/Qualifiers
source                    1..20
                          mol_type = other DNA
                          organism = synthetic construct
SEQUENCE: 2
gttgttgttg gtctggatgc                                                    20

SEQ ID NO: 3              moltype = DNA   length = 19
FEATURE                   Location/Qualifiers
source                    1..19
                          mol_type = other DNA
                          organism = synthetic construct
SEQUENCE: 3
gcccttgtcc ctgtcccta                                                     19

SEQ ID NO: 4              moltype = DNA   length = 24
FEATURE                   Location/Qualifiers
source                    1..24
                          mol_type = other DNA
                          organism = synthetic construct
SEQUENCE: 4
gcagagtatt tccctttggt ttga                                               24

SEQ ID NO: 5              moltype = DNA   length = 21
FEATURE                   Location/Qualifiers
source                    1..21
                          mol_type = other DNA
                          organism = synthetic construct
SEQUENCE: 5
actggaacgg tgaaggtgac a                                                  21

SEQ ID NO: 6              moltype = DNA   length = 22
FEATURE                   Location/Qualifiers
source                    1..22
                          mol_type = other DNA
                          organism = synthetic construct
SEQUENCE: 6
atggcaaggg acttcctgta ac                                                 22
```

COMBINATION THERAPY FOR TREATING CANCER

CROSS-REFERENCE TO RELATED APPLICATION

This application claims the benefit of U.S. Provisional Application No. 63/321,185, filed Mar. 18, 2022, the disclosure of which is hereby incorporated by reference in its entirety.

SEQUENCE LISTING

This application contains a sequence listing, which is submitted electronically via Patent Center as an XML formatted sequence listing with a file name "211106US-sequence listing-jc-20230320.xml", created on Mar. 20, 2023, file size of 7 kb. The sequence listing submitted via Patent Center is part of the specification and is herein incorporated by reference in its entirety.

TECHNICAL FIELD

The present disclosure relates to methods for the treating proliferative diseases, particularly to the method for treating cancer by a combination therapy.

DESCRIPTION OF THE RELATED ART

There were an estimated 18.1 million cancer cases around the world in 2020. By 2040, the global burden is expected to grow to 27.5 million new cancer cases and 16.3 million cancer deaths.

There are approximately more than 700 oncology drugs, and more are still developing. Chemotherapy is one of the common cancer treatments that involves the disruption of cell metabolism and can be more effective than other treatment choices, but the resistance can occur as the individual's genetic differences, especially in tumor somatic cells. Also, once the cancer drug resistance is acquired, the drug resistance can be occurred by different mechanism, for example, cell death inhibiting, and gene amplification. For example, cisplatin is a broad-spectrum anticancer chemotherapeutic agent. However, cisplatin resistance represents a problem for treatment which includes insufficient DNA binding, increased detoxification, increased DNA repair, deregulated expression of transporters, and altered expression and activation of genes involved in cell death pathways, such as p53, Bcl-2, and Akt/mTOR. Gemcitabine is other chemotherapy drug used as a treatment for different types of cancer. However, most cancer patients receiving gemcitabine chemotherapy also eventually develop resistance to gemcitabine which includes alteration of gemcitabine metabolism, decreased intracellular drug accumulation, inhibition of apoptosis pathways and aberrant activity in signaling pathways that modulate the cell cycle and apoptosis. Pemetrexed is another chemotherapy drug improves the overall survival of patients with cancer; however, pemetrexed resistance also often appears during the therapy.

Other forms of therapies such as radiation, hormone therapy, and surgery are often unresponsive and ineffective.

As arsenal of targeted anticancer drugs increases, despite the promise observed in preclinical experiments and initial high response rates, a large number of targeted drugs has not been successful in providing reproducible improvements in survival in patients with cancer when used as single agents. Also, recognizing treatment-induced toxicity and the inability to use continuous pharmacodynamically effective doses of many targeted treatments needs creative intermittent scheduling.

Since the treatment of cancer is still unsatisfied, there is a clear unmet medical need for additional cancer treatment agents in cancer patients.

SUMMARY

In view of the above-mentioned problems in the technical field, the present disclosure provides effective methods for the treatment of proliferative diseases such as cancer.

The present disclosure provides a method of treating cancer comprising administering a therapeutically effective amount of a pharmaceutical composition and a chemotherapy agent to a subject in need thereof, wherein the pharmaceutical composition comprises a benzenesulfonamide derivative and a pharmaceutically acceptable carrier thereof, and the chemotherapy agent comprises at least one selected from the group consisting of an alkylating agent, an antimetabolite, and a corticosteroid.

In at least one embodiment of the present disclosure, the benzenesulfonamide derivative is represented by formula (I) below:

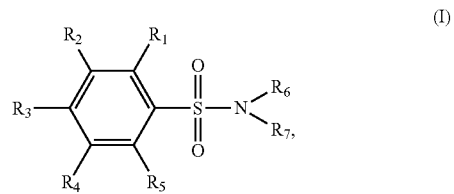

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and wherein the alkyl, alkoxy, cycloalkyl, cycloheteroalkyl groups and the ring in $R_1$ to $R_7$ are independently unsubstituted or substituted with one or more substituents.

In at least one embodiment of the present disclosure, the substituent is selected from the group consisting of phenyl, halo, oxo, ether, hydroxyl, carboxyl, amino, sulfo and sulfonamide group.

In at least one embodiment of the present disclosure, the benezesulfonamide derivative or the pharmaceutically acceptable salt thereof is at least one selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide,

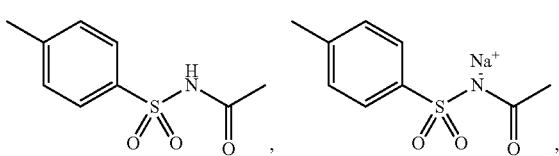

-continued
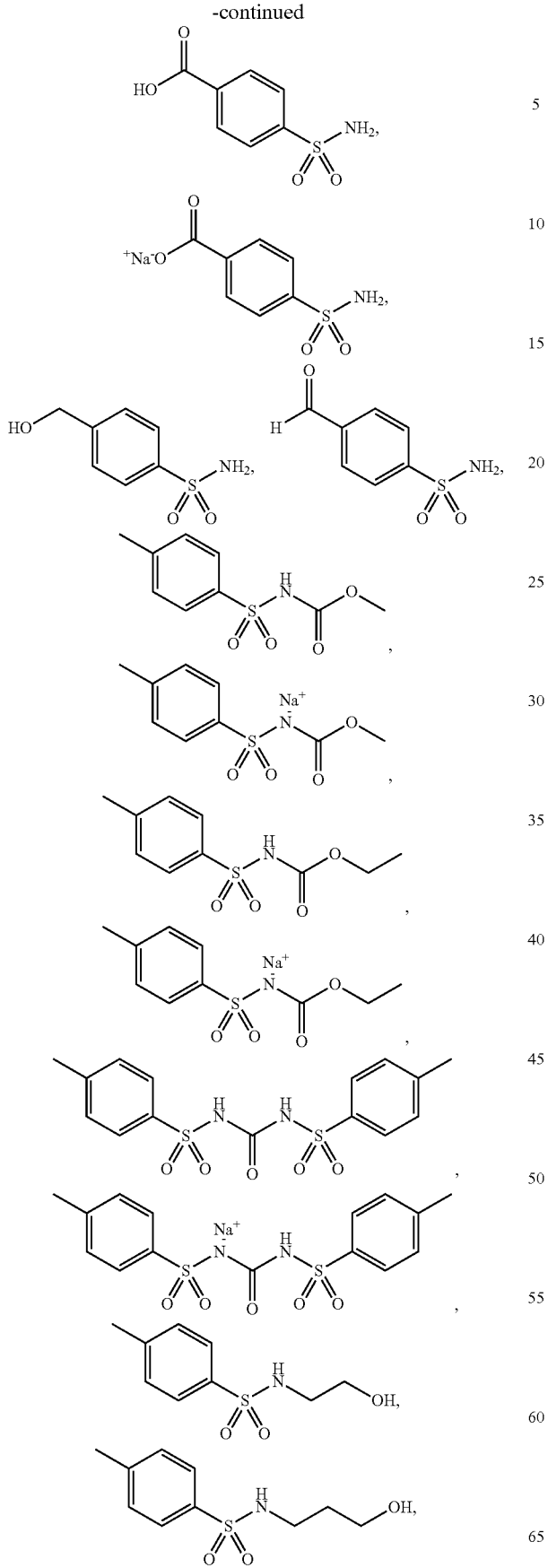
-continued
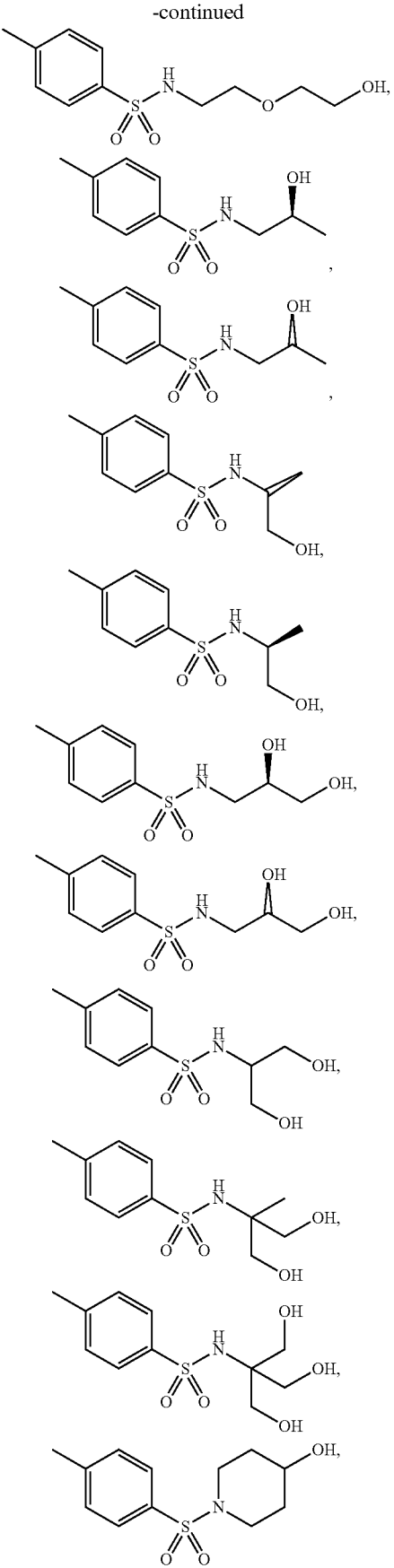

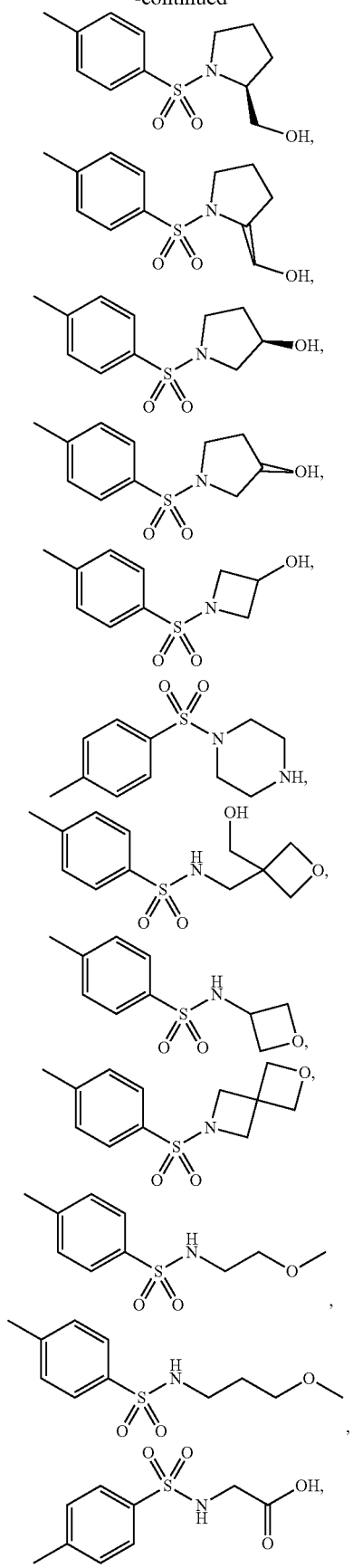
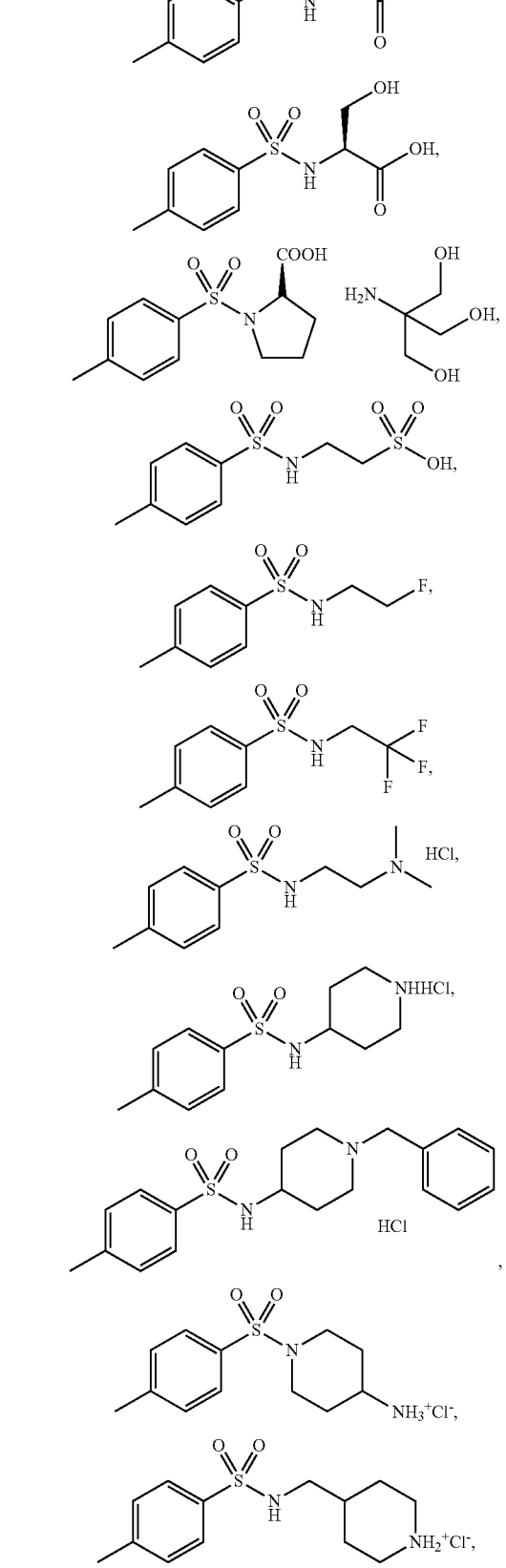

-continued

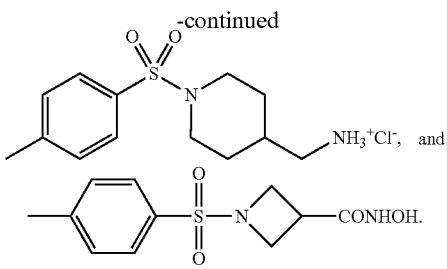

In at least one embodiment of the present disclosure, the alkylating agent is cisplatin.

In at least one embodiment of the present disclosure, the antimetabolite is gemcitabine or pemetrexed.

In at least one embodiment of the present disclosure, the cancer is a melanoma or lung cancer.

In at least one embodiment of the present disclosure, the cancer is melanoma, and the chemotherapy agent comprises cisplatin. In some embodiments, a ratio of the benzenesulfonamide derivative to the cisplatin is in a range of 25:1 to 2000:1. In some embodiments, the benzenesulfonamide derivative is administered to the subject at a dosage of about 100 mg/kg, and the cisplatin is administered to the subject at a dosage of about 2 mg/kg.

In at least one embodiment of the present disclosure, the cancer is lung squamous cell carcinoma, and the chemotherapy agent comprises gemcitabine and cisplatin. In some embodiments, a ratio of the benzenesulfonamide derivative to the gemcitabine is in a range of 1.5:1 to 100:1, and a ratio of the benzenesulfonamide derivative to the cisplatin is in a range of 25:1 to 2000:1. In some embodiments, the benzenesulfonamide derivative is administered to the subject at a dosage of about 330 mg/kg, the gemcitabine is administered to the subject at a dosage of about 160 mg/kg, and the cisplatin is administered to the subject at a dosage of about 3 mg/kg.

In at least one embodiment of the present disclosure, the cancer is lung adenocarcinoma, and the chemotherapy agent comprises pemetrexed and cisplatin. In some embodiments, a ratio of the benzenesulfonamide derivative to the pemetrexed is in a range of 1.5:1 to 100:1, and a ratio of the benzenesulfonamide derivative to the cisplatin is in a range of 25:1 to 2000:1. In some embodiments, the benzenesulfonamide derivative is administered to the subject at a dosage of about 330 mg/kg, the pemetrexed is administered to the subject at a dosage of about 100 mg/kg, and the cisplatin is administered to the subject at a dosage of about 2 mg/kg.

In at least one embodiment of the present disclosure, the ratio of the benzenesulfonamide derivative is administered to the subject at a dosage of about 330 mg/kg, the pemetrexed is administered to the subject at a dosage of about 100 mg/kg, and the cisplatin is administered to the subject at a dosage of about 2 mg/kg.

In at least one embodiment of the present disclosure, the benzenesulfonamide derivative in the pharmaceutical composition is administered to the subject in an effective amount of from about 3,300 mg to about 26,400 mg.

In at least one embodiment of the present disclosure, the benzenesulfonamide derivative in the pharmaceutical composition is administered to the subject in an effective amount of from about 165 mg to about 6,600 mg per day.

In at least one embodiment of the present disclosure, the pharmaceutical composition or the chemotherapy agent is administered to the subject one time to three times a week. In some embodiments, the pharmaceutical composition is administered to the subject two times a week, and the chemotherapy agent is administered to the subject one time a week.

In at least one embodiment of the present disclosure, the pharmaceutically acceptable carrier is selected from the group consisting of a filler, a binder, a preservative, a disintegrating agent, a lubricant, a suspending agent, a wetting agent, a flavoring agent, a thickening agent, an acid, a biocompatible solvent, a surfactant, a complexation agent, and any combination thereof.

In at least one embodiment of the present disclosure, the pharmaceutically acceptable carrier is selected from the group consisting of polyethylene glycol, alkylene glycol, propylene glycol, sebacic acid, dimethyl sulfoxide, ethanol, and any combination thereof.

In at least one embodiment of the present disclosure, the pharmaceutical composition is in a form selected from the group consisting of a formulation to injection, dry powder, a tablet, an oral liquid, a wafer, a film, a lozenge, a capsule, a granule, a pill, a gel, a lotion, an ointment, an emulsifier, a paste, a cream, an eye drop, and a salve.

In at least one embodiment of the present disclosure, the pharmaceutical composition or the chemotherapy agent is administered to the subject intratumorally, intravenously, subcutaneously, intradermally, orally, intrathecally, intraperitoneally, intranasally, intramuscularly, intrapleuraly, topically, or through nebulization.

In at least one embodiment of the present disclosure, the subject is a human, a dog, a cat, or a mouse.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will become more readily appreciated by reference to the following descriptions in conjunction with the accompanying drawings.

FIG. 1A is an image that shows tumors excised from the mice 28 days after tumor-cell implantation. FIG. 1B is a graph shows changes in tumor volume over time. Treatments were administered from day 7 (when the tumors were detected) three times per week (except for the control, which was administered daily), as follows: saline (control); 2 mg/kg cisplatin (cisplatin); 100 mg/kg PTS (PTS); and 100 mg/kg PTS combined with 2 mg/kg cisplatin (cisplatin+PTS). Data presented are mean±standard deviation (SD), n=7 per group. ***$p<0.05$ vs control; #$p<0.05$ vs cisplatin; +$p<0.05$ vs PTS.

FIG. 2A is a set of color staining with DAPI, TUNEL, and the two merged. FIG. 2B is a percentage of cells in the tumors that were TUNEL-positive in control mice and those administered with one of the following treatments three times per week (except for the control, which was administered daily), starting on day 7 (when the tumors were detected): saline (control), 2 mg/kg cisplatin (cisplatin); 100 mg/kg PTS (PTS); or 100 mg/kg PTS and 2 mg/kg cisplatin (cisplatin+PTS). Data are mean±SD, n=7 per group. $p<0.01$, *$p<0.001$ vs control; ####$p<0.001$ vs cisplatin; +++$p<0.001$ vs PTS. Scale bars: 50 μm; magnification: 200×.

FIG. 3A is a representative western blot. FIG. 3B is a quantitative comparison of the expression of cleaved caspase 3. FIG. 3C is a quantitative comparison of the expression of phosphorylated Erk. FIG. 3D is a quantitative comparison of the expression of Bcl-2. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. *$p<0.05$, $p<0.01$; and *$p<0.001$ vs control; #$p<0.05$ and ##$p<0.01$ vs cisplatin, ++$p<0.01$ vs PTS.

FIG. 4A is a set of color representative images showing IL-1 expression. FIG. 4B is a set of color representative image showing TNF-α expression. FIG. 4C is a quantitative analysis of IHC expression IL-1β. FIG. 4D is a quantitative analysis of IHC expression TNF-α. FIG. 4E is a quantitative analysis of IHC expression serum IL-6. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. $p<0.01$; and *$p<0.001$ vs control; $p<0.01$ vs cisplatin; and ++$p<0.01$ vs PTS. Scale bars: 50 μm.

FIG. 5A shows a representative western blot of COX-2. FIG. 5B shows a quantitative comparison of COX-2 expression in the four treatment groups (control, cisplatin, PTS, and cisplatin+PTS). A quantitative polymerase chain reaction (PCR) was conducted to assess the relative mRNA expression levels of NF-κB in FIG. 5C and expression level of 1κBα. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. $p<0.01$ and *$p<0.001$ vs control; #$p<0.05$ and ##$p<0.01$ vs cisplatin; +$p<0.05$ and ++$p<0.01$ vs PTS.

FIGS. 6E to 6G show representative western blot (FIG. 6E) from analysis of the relative expression of EGFR (FIG. 6F) and VEGF (FIG. 6G). The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. *$p<0.05$,  $p<0.01$ and $p<0.001$ vs control; ##$p<0.01$ vs cisplatin; ++$p<0.01$ vs PTS. Scale bars: 50 μm.

FIG. 7A is a representative western blot of mTOR and S6K1 expression. FIGS. 7B and 7C show quantification of the relative expression levels of mTOR phosphorylation (FIG. 7B) and S6K1 phosphorylation (FIG. 7C). The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. *$p<0.05$, $p<0.01$ and *$p<0.001$ vs control; #$p<0.05$ vs cisplatin; +$p<0.05$ vs PTS.

FIG. 9A is a set of color representative IHC images indicating Ki67 expression. FIG. 9B is a quantitative comparison of expression level of Ki67. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. *$p<0.05$ and ***$p<0.001$ vs control; ##$p<0.01$ vs cisplatin; ++$p<0.01$ vs PTS. Scale bars: 50 μm.

FIG. 11A is a set of color representative IHC images indicating CD45 expression. FIG. 11B is a quantitative comparison of expression levels of CD45. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. * $p<0.05$ and ** $p<0.01$ vs control; #$p<0.05$ vs cisplatin; +$p<0.05$ vs PTS. The scale bars of FIG. 11A is 50 μm.

FIG. 12A shows changes in tumor volume over time in 4 groups: control, PTS, gemcitabine+cisplatin (G+C) and gemcitabine+cisplatin+PTS (G+C+P). FIG. 12B is a shows tumor weight in 4 groups: control, PTS, GEM+CDDP and GEM+CDDP+PTS. FIG. 12C shows a combination index (CI) plot and the combination value is plotted as a function of Fa for a set of 3 drugs combination (G+C+P) in first experiment.

FIG. 13A shows changes in tumor volume over time in 4 groups: control, PTS, gemcitabine+cisplatin (GEM+CDDP) and gemcitabine+cisplatin+PTS (GEM+CDDP+PTS). FIG. 13B is a shows tumor weight in 4 groups: control, PTS, GEM+CDDP and GEM+CDDP+PTS. FIG. 13C shows a combination index (CI) plot and the combination value is plotted as a function of Fa for a set of 3 drugs combination (G+C+P) in first experiment.

FIG. 14A shows changes in tumor volume over time in 4 groups: control, PTS (330 mg/kg), Cisplatin (2 mg/kg)+pemetrexed (100 mg/kg) and combination (PTS+Cisplatin+Pemetrexed). FIG. 14B shows changes in tumor weight over time in control, PTS, CDDP+ Pemetrexed and All (PTS+CDDP+Pemetrexed). FIG. 14C shows a combination index (CI) plot and the combination value is plotted as a function of Fa for a set of 3 drugs combination (PTS+Cisplatin+Pemetrexed).

DETAILED DESCRIPTIONS OF THE EMBODIMENTS

Figure 1A:
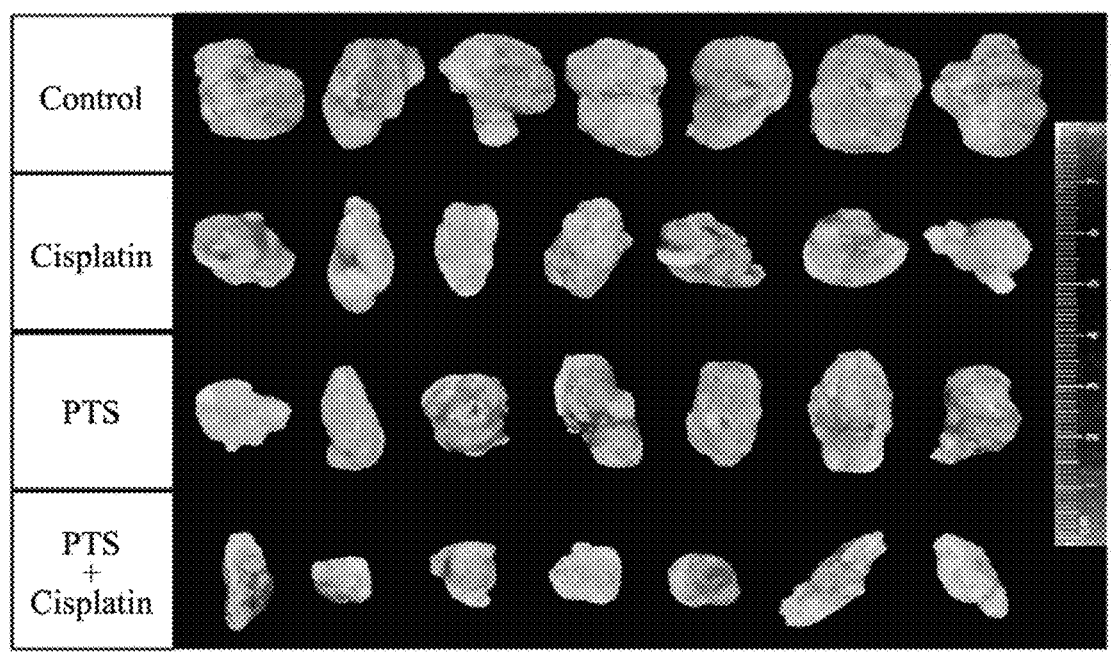
FIGS. 1A to 1B show effects of treatment with cisplatin, PTS, and the two combined on M5 melanoma tumor growth in BALB/c nude mice.

The following embodiments are provided to illustrate the present disclosure in detail. A person having ordinary skill in the art can easily understand the advantages and effects of the present disclosure after reading the disclosure of this specification, and also can implement or apply in other different embodiments. Therefore, it is possible to modify and/or alter the following embodiments for carrying out this disclosure without contravening its scope for different aspects and applications, and any element or method within the scope of the present disclosure disclosed herein can combine with any other element or method disclosed in any embodiments of the present disclosure.

As used herein, the singular forms "a," "an," and "the" include plural referents unless expressly and unequivocally limited to one referent. The term "or" is used interchangeably with the term "and/or" unless the context clearly indicates otherwise.

As used herein, the term "tumor" refers to any malignant form of cancer that arises from melanocytes. For example, the melanoma may include, but is not limited to, mucosal melanoma, acral melanoma, ocular melanoma, cutaneous melanoma, superficial spreading melanoma, nodular melanoma, polypoid melanoma, lentigo maligna melanoma, desmoplastic melanoma, soft-tissue melanoma, amelanotic melanoma, juvenile melanoma, Harding-Passey melanoma, subungual melanoma, spitzoid melanoma, blue nevus-like melanoma, or any combination thereof. The melanoma may also include, but is not limited to, metastatic melanoma. Ultraviolet (UV) radiation status, epidemiology, histopathological features, genetics, prognosis, and outcomes may be different between these subtypes of melanomas.

As used herein, the term "combination" means any combination of the PTS with other chemotherapy agent including, but not limited to, cisplatin (abbreviated as C or CDDP), gemcitabine (abbreviated as G or GEM), pemetrexed, or any types of alkylating agents (e.g., bendamustine, chlorambucil, cyclophosphamide, ifosfamide, mechlorethamine, melphalan, carmustine, lomustine, streptozocin, busulfan, dacarbazine, temozolomide, altretamine, or thiotepa), or any types of antimetabolites agents (e.g., 6-mercaptopurine, fludarabine, 5-fluorouracil, gemcitabine, cytarabine, pemetrexed, methotrexate), or any types of corticosteroid.

The numeral ranges used herein are inclusive and combinable, any numeral value that falls within the numeral scope herein could be taken as a maximum or minimum value to derive the sub-ranges therefrom. For example, it should be understood that the numeral range "1-60%" comprises any sub-ranges between the minimum value of 1% to the maximum value of 60%, such as the sub-ranges from 1% to 50%, from 10% to 60%, and from 20.5% to 40.5%.

The term "about" as used herein when referring to the numerical value is meant to encompass variations of ±20%, ±10%, ±5%, ±1%, ±0.5%, or ±0.1% from the numerical value. Such variations in the numerical value may occur by, e.g., the experimental error, the typical error in measuring or handling procedure for making compounds, compositions, concentrates, or formulations, the differences in the source, manufacture, or purity of starting materials or ingredients used in the present disclosure, or like considerations.

As used herein, "subject" may encompass any vertebrate including, but not limited to, humans, mammals, reptiles, amphibians, and/or fish. However, advantageously, the subject is a mammal such as a human, or an animal mammal such as a domesticated mammal, e.g., a dog, a cat, a horse, or the like, or a production mammal, e.g., a cow, a sheep, a pig, or the like.

As used herein, the terms "comprise," "comprising," "include," "including," "have," "having," "contain," "containing," and any other variations thereof are intended to cover a non-exclusive inclusion. For example, when describing an object "comprises" a limitation, unless otherwise specified, it may additionally include other ingredients, elements, components, structures, regions, parts, devices, systems, steps, or connections, etc., and should not exclude other limitations.

As used herein, the term "melanoma" refers to any malignant form of cancer that arises from melanocytes. For example, the melanoma may include, but is not limited to, mucosal melanoma, acral melanoma, ocular melanoma, cutaneous melanoma, superficial spreading melanoma, nodular melanoma, polypoid melanoma, lentigo maligna melanoma, desmoplastic melanoma, soft-tissue melanoma, amelanotic melanoma, juvenile melanoma, Harding-Passey melanoma, subungual melanoma, spitzoid melanoma, blue nevus-like melanoma, or any combination thereof. The melanoma may also include, but is not limited to, metastatic melanoma. Ultraviolet (UV) radiation status, epidemiology, histopathological features, genetics, prognosis, and outcomes may be different between these subtypes of melanomas.

Example

Exemplary embodiments of the present disclosure are further described in the following examples, which should not be construed to limit the scope of the present disclosure.

Preparation Example

Pharmaceutical Composition of p-Toluenesulfonamide (PTS):

| | |
|---|---|
| p-Toluenesulfonamide | 1%-60% |
| PEG-400 | 10%-40% |
| 1,2-Propylene glycol | 5%-10% |
| Sebacic acid | 1%-5% |
| p-Toluenesulfonic acid | 0%-15% |
| 2-Ethyl-1,3-hexanediol | 10%-20% |
| Dimethyl sulfoxide | 0-10% |
| Ethanol | 0-20% | p-Toluenesulfonamide is a small organic compound used as a local therapeutic drug that is injected directly into the tumors and has been shown to induce cancer cell death by activating apoptosis and necrosis in hepatocellular carcinoma, non-small-cell lung cancer, and tongue squamous cell carcinoma. The present disclosure also provides the use of the PTS composition as a medicament for treating cancer.

Preparation of the PTS composition of the present disclosure includes the process of: adding and mixing the solvents and adjuvants in a given ratio; heating the mixture to 80° C. to 110° C. with stirring to form a clear oily liquid; gradually adding the sulfa drug with stirring until completely dissolved; filtering and cooling the mixture to obtain the composition of the present disclosure in an oily liquid form.

The preparation of the PTS composition injection may be conducted by some techniques known in the art, e.g., adding an adjuvant and/or solvent to adjust the mixture to an isotonic state, or filtering the mixture by using a microporous filter.

In the following experimental designs, the drugs are used in combination to cause measurable tumor regressions when employed individually, each may or may not to demonstrate a different mechanism of action to minimize the development of resistance, the clinical toxicities of each compound are not overlapped to permit their use in effective doses, and intensive intermittent treatment is preferred over continuous, low-dose therapy to enhance removal of tumors.

Experimental Design I

Co-Effect of PTS and Cisplatin for the Treatment of Canine Melanoma

Materials and Methods

Animals and Cell Line

Male BALB/cByJNarl mice at six-weeks of age were obtained from National Laboratory Animal Breeding and Research Center, Taipei, Taiwan. Two mice were housed in each cage and provided them with sterile food and water. The mice were maintained under a constant temperature (22±2° C.) and relative humidity (55±5%), with a 12:12 h light:dark cycle. The Institutional Animal Care and Use Committee (IACUC) at the National Chiayi University (IACUC Approval No.110003) reviewed and approved the study protocol, in which procedures were in accordance with the Guidelines for the Care and Use of Laboratory Animals published by the Taiwanese Ministry of Health and Welfare.

The M5 canine melanoma cell line was obtained from the School of Veterinary Medicine at National Taiwan University. The cells were cultured in a humidified atmosphere (95% air, 5% $CO_2$) at 37° C. in 90% high-glucose Dulbecc's Modified Eagle Medium supplemented with 5% fetal bovine serum, 50 IU/ml of penicillin, and 50 mg/ml of streptomycin (Gibco Laboratories, Grand Island, NY, USA). The cells were routinely passaged by removing the medium and overlaying the cell monolayer with 0.25% trypsin and 0.1% ethylenediaminetetraacetic acid.

Inoculation and Treatment of Tumors

The experimental treatments were commenced after the implanted M5 cells had formed a detectable tumor mass, which was assessed on day 7 after implantation. Briefly, the mice were anesthetized via intraperitoneal injection of Zoletil (Virbac Taiwan, Taipei, Taiwan), and then subcutaneously injected 100 µl of cell suspension containing $10^7$ viable M5 cells into a posterior leg. The development of the tumor lesions was assessed on day 7, and randomly divided the animals that showed a distinct tumor 4 to 5 mm in diameter into four groups (7 mice per group). All treatments were administered via intraperitoneal injection. The control group received saline daily, while the three treatment groups received their corresponding treatments three times per week. The cisplatin group received 2 mg/kg cisplatin (Sigma; St. Louis, MO, USA). The PTS group was administered with 100 mg/kg PTS (Gongwin Biopharm Holding, Taipei, Taiwan). The cisplatin+PTS group received 100 mg/kg PTS and 2 mg/kg cisplatin. The dosage of cisplatin was selected such that this drug affects apoptosis, invasion, metastasis, angiogenesis, and the growth signal mechanisms in canine melanoma implanted in mice. The PTS dosage was based on the dose that is generally used to treat lung cancer, for example, at 220, 230, 240, 250, 260, 270, 280, 290, 300, 310, 320, 330, 340, 350, 360, 370, 380, 400, 500, 600 700, 800 mg/kg. The growth of the tumors was assessed every seven days by measuring their largest and smallest diameters, and calculated their volume according to the following formula: $V=0.5 \times a \times b^2$, where a and b are the largest and smallest diameters, respectively.

Clinical Observations and Histopathological Analysis

The mice were observed daily for clinical signs, weighed them every three days, and at one month after tumor-cell implantation euthanized them with an overdose of anesthetic combined with carbon dioxide. Immediately before sacrificing the mice, the blood was collected from them under anesthesia for hematological assessment. After euthanizing the mice, the tumors were excised immediately. The tumor specimens were divided into two groups. One group was treated with 10% formalin and embedded the specimens in paraffin. These specimens were investigated by hematoxylin and eosin staining; terminal deoxyribonucleotidyl transferase (TdT)-mediated biotin-16-dUTP nick-end labeling (TUNEL assay; APO-BrdU TUNEL Assay Kit, BD Pharmingen, San Diego, CA, USA); and IHC for IL-1β, TNF-α, TGF-β, and CD44, using primary antibodies against these factors (Merck, Billerica, MA, USA). Protein expression was assessed via IHC with the TAlink mouse/rabbit polymer detection system produced by BioTnA (Kaohsiung, Taiwan). A high-resolution digital microscope (Moticam 2300, Motic Instruments, Richmond, Canada) equipped with Motic Images Plus (version 2.0) was used to capture and analyze the images. The other groups of tumor specimens were first minced coarsely and homogenized, and then stored in a freezer at −80° C. These groups of tumor specimens were subjected to western blotting for analyzing expression of cleaved caspase 3, ERK, Bcl-2, COX-2, VEGF, and EGFR.

Measurement of Serum Levels of IL-6

The serum levels of IL-6 in the blood samples were measured using commercial mouse kits (ab213749 and ab100697; Abcam, Cambridge, MA, USA) according to the manufacturer's protocol. 50 µl of samples were added to each of the wells in 96-well antibody-coated plates and then incubated for 2 hours at room temperature. 50 µl of the detector antibody solution was loaded into each well and incubated the plates for a further 1 hour at room temperature. Next, 50 µl of HRP-Streptavidin solution (ab210901, Abcam) was added to each well, and once again incubated the plates for 1 hour at room temperature. Finally, 100 µl of tetramethylbenzidine substrate was added to each well and incubated the plates for another 10 min in the dark, again at room temperature. The reaction was stopped by adding 100 µl of stop solution. The wavelength of absorbance was at 450 nm and results were expressed in pg/ml.

RNA Extraction and Real-Time Quantitative Polymerase Chain Reaction (PCR)

TRI Reagent (Sigma) was used to extract total RNA from the tumor tissues. The concentrations of RNA were quantified based on absorbance at 260 to 280 nm and 230 to 260 nm using a Qubit fluorometer (Invitrogen, Carlsbad, CA, USA). 1 μg of the RNA was reverse-transcribed into cDNA using an iScript cDNA synthesis kit (Bio-Rad, Hercules, CA, USA) according to the manufacturer's instructions. Real-time PCR was performed using the cDNA and iTaq universal SYBR Green supermix (Bio-Rad), according to the manufacturer protocol. The mRNA expression levels of NF-κB and IκBα were quantified using the CFX Connect Real-Time PCR Detection System (Bio-Rad). The following settings were used for the PCR: 40 cycles of 95° C. for 30 s; 95° C. for 15 s, and 60° C. for 30 s; and a final 5 min at 72° C. We used the following sequence primers for NF-κB, IκBα, and β-actin: NF-κB forward, 5'-ATGGCTTCTAT-GAGGCTGAG-3' (SEQ ID NO. 1), and reverse, 5'-GTTGTTGTTGGTCTGGATGC-3' (SEQ ID NO. 2); IκBα forward, 5'-GCCCTTGTCCCTGTCCCTA-3' (SEQ ID NO. 3), and reverse, 5'-GCAGAG-TATTTCCCTTTGGTTTGA-3' (SEQ ID NO. 4); and β-actin forward, 5'-ACTGGAAC-GGTGAAGGTGACA-3' (SEQ ID NO. 5), and reverse, 5'-ATGGCAAGGGACTTCCTGTAAC-3' (SEQ ID NO. 6). The levels of expression were calculated for the two target genes relative to the β-actin levels studied and expressed them using the $2^{-\alpha\alpha Ct}$ method.

Western Blotting

Western blotting on the second group of tumor specimens was performed according to standard protocol (Wu et al 2020). Antibodies was used against β-actin, Bcl-2, COX-2, VEGF, and EGFR (Sigma) and against cleaved caspase 3, phosphorylated ERK (threonine 202/tyro-sine 204), and ERK (Cell Signaling Technology, Beverly, MA, USA). Enhanced chemiluminescence reagents were used (Thermo Scientific, Rockford, MA, USA) to assess immunoreactivity and UVP ChemStudio (Analytik Jena, Upland, CA, USA) to detect the signal. Protein expression and phosphorylation were quantified with ImageJ (National Institutes of Health, Bethesda, MA, USA).

Statistical Analysis

All data were expressed as mean±standard deviation. T-tests was used to access for significant differences between pairs of groups. When comparing more than two groups, an analysis of variance (ANOVA) with a post hoc Bonferroni correction was performed. P-values below 0.05, 0.01, and 0.001 were considered significant, very significant, and extremely significant, respectively.

Tumor Growth is Restricted by PTS

Figure 1B:
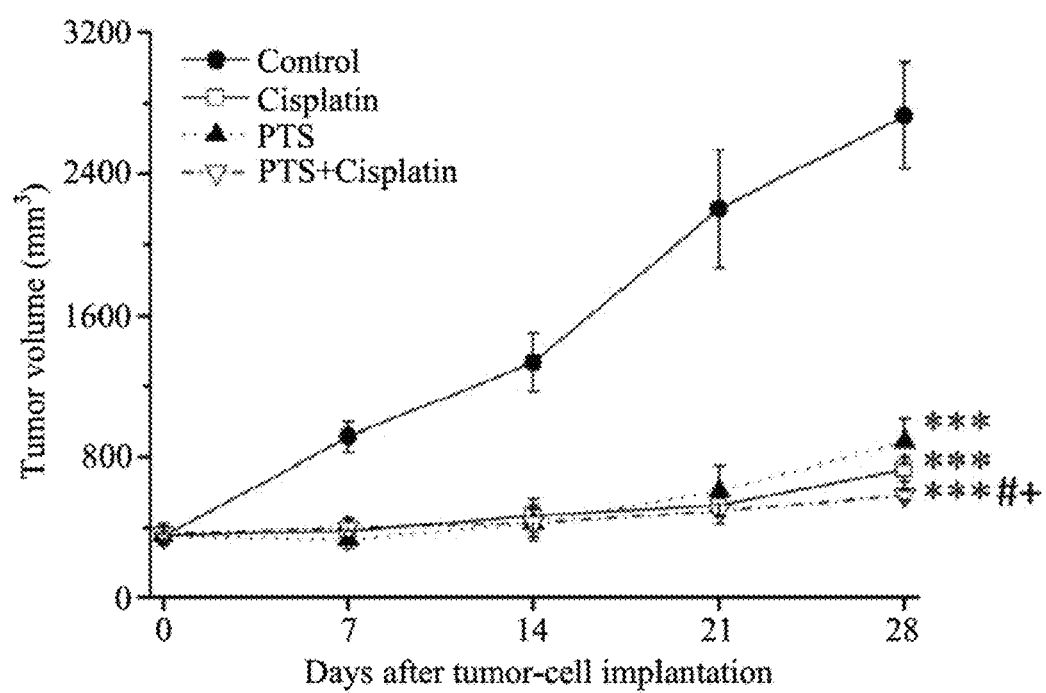

Treatment with cisplatin and PTS (whether used individually or combined) led to smaller tumor size and volume relative to the control group (FIG. 1A). Further, the time course analysis showed that tumor growth was significantly retarded by all three treatments (p<0.001) relative to the control (FIG. 1B). These effects were strongest when PTS and cisplatin were used together: cisplatin alone reduced tumor mass by 48.7%, PTS alone reduced it by 44.2%, and a combination of cisplatin with PTS reduces the tumor mass by at least 72.8% relative to the control (Table 1). Canine melanoma growth is thus strongly inhibited by treatment with both PTS and cisplatin.

TABLE 1

Tumor masses after excision from sacrificed BALB/cBy JNarl Mice

| | Tumor mass (g) | Tumor mass reduction (%) |
|---|---|---|
| Control | 2.67 ± 0.32 | — |
| Cisplatin | 1.37 ± 0.25*** | 48.7 |
| PTS | 1.48 ± 0.33*** | 44.2 |
| PTS + cisplatin | 0.72 ± 0.19***#+ | 72.8 |

Figure 2A:
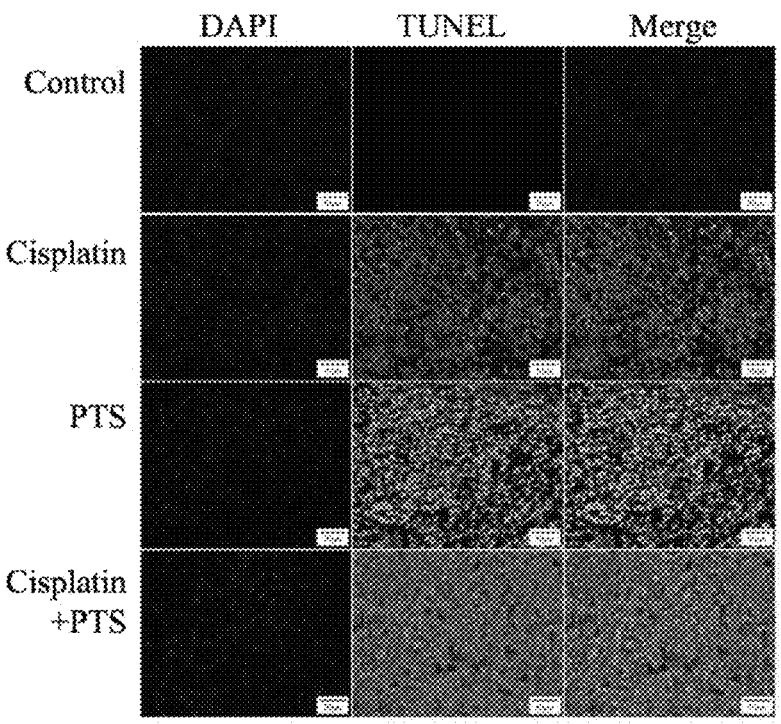
FIGS. 2A to 2B show TUNEL/DAPI assay of apoptosis in M5 canine melanoma tumor implanted in BALB/c nude mice.
Figure 2B:
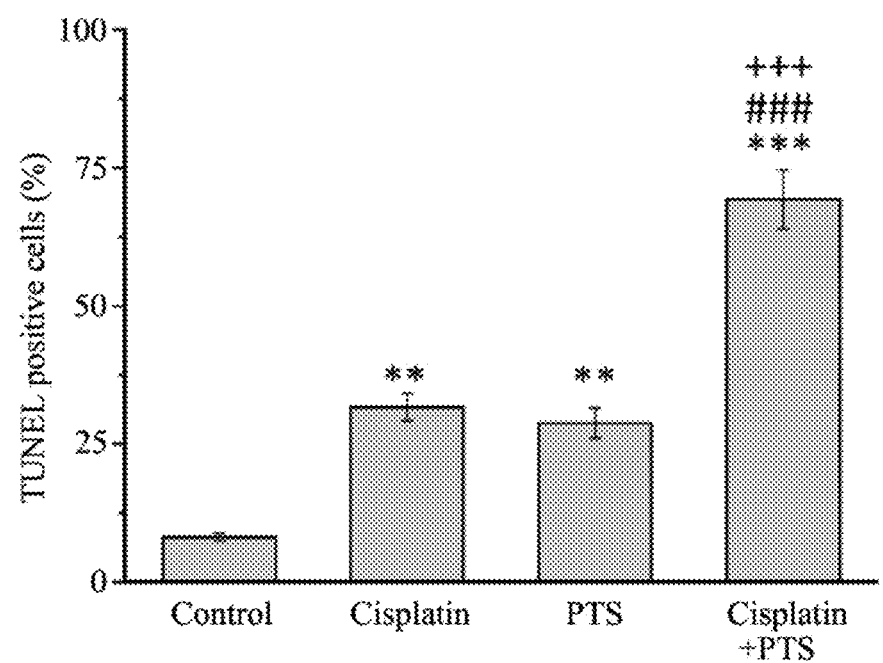

Data are mean ± SD.
***P < 0.001 vs control;
p < 0.05 vs cisplatin;
+p < 0.05 vs PTS Abundance of TUNEL-Positive Cells Increases in Response to PTS In at least one embodiment of the present disclosure, an essential aspect of the growth and survival of all organisms is apoptosis, which is programmed cell death. In the later stages of apoptosis, the dying cells' DNA becomes substantially degraded, and cells with this degraded DNA can be detected using a TUNEL assay. The TUNEL assay revealed that all three treatments resulted in a greater abundance of apoptotic cells: in the cisplatin group, the TUNEL-positive cell count was 3.9 times that of the control (p<0.01); in the PTS group this ratio was 3.5 (p<0.01); and in the cisplatin+ PTS group was 8.6 (p<0.001; FIGS. 2A and B). The difference between the PTS and cisplatin groups was not significant, but that between the combined treatment group and the other two treatment groups was substantial and significant (p<0.001). Thus, all three treatments enhanced apoptosis. Importantly, the combination treatment enhanced the anti-tumor activity of PTS in this model. This effect was most prominent in the group with PTS in addition of cisplatin, which was far more effective than PTS or cisplatin alone.

Expression of Apoptosis-Associated Proteins is Affected by PTS Treatment

Figure 3A:
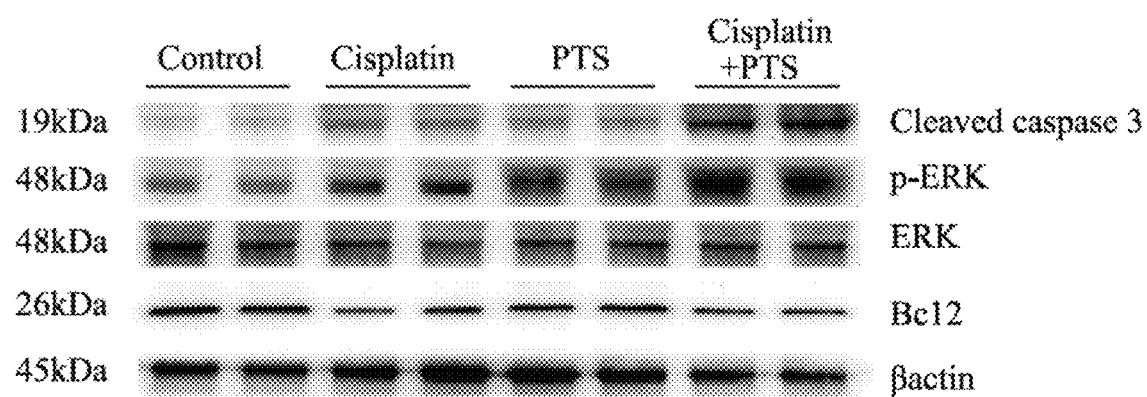
FIGS. 3A to 3D show results of Western blot analysis of apoptosis-related proteins in M5 canine melanoma tumors implanted in BALB/c nude mice.
Figure 3B:
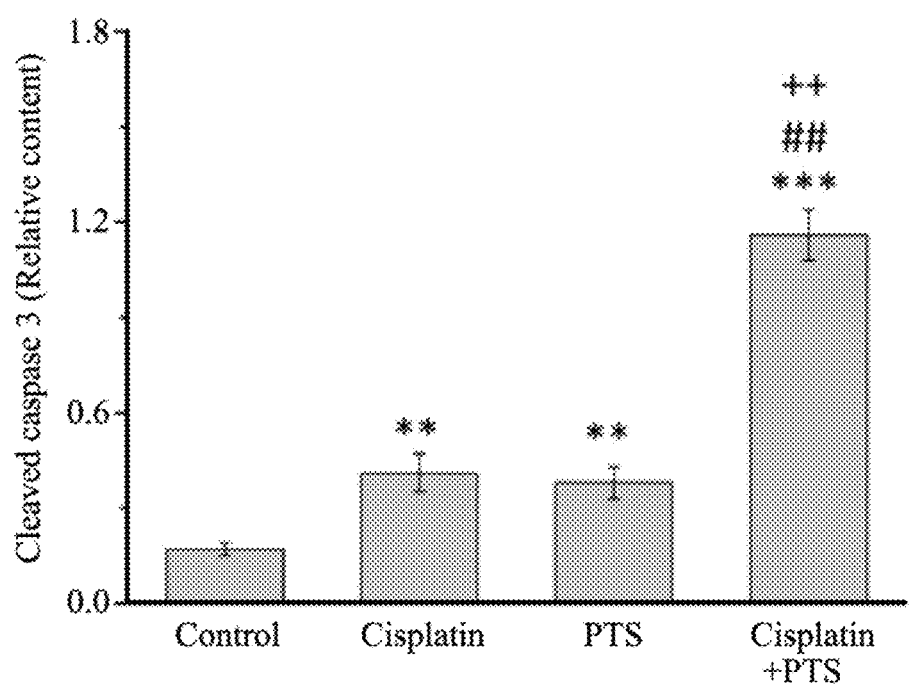
Figure 3C:
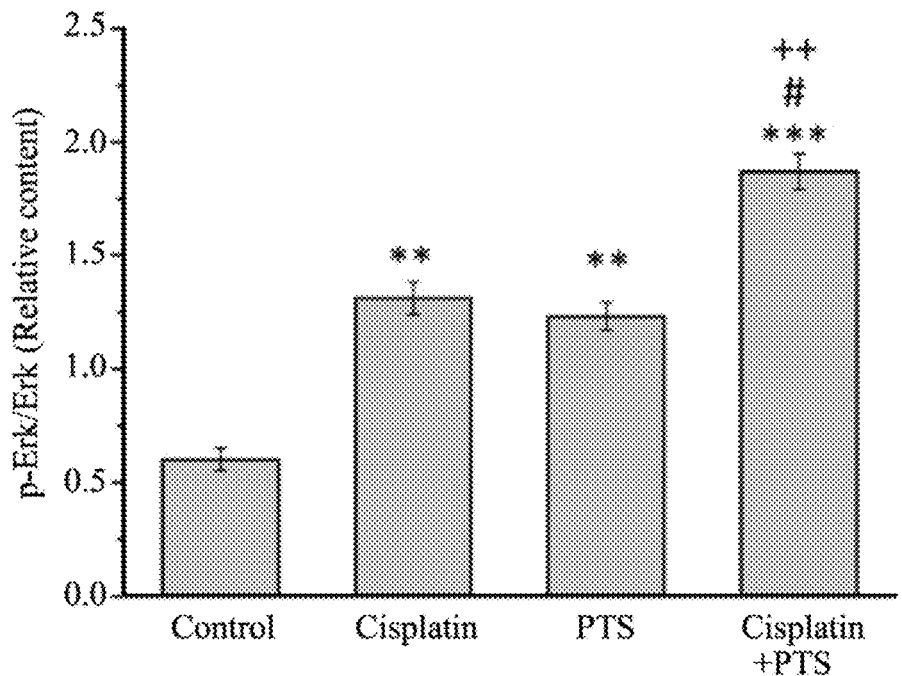
Figure 3D:
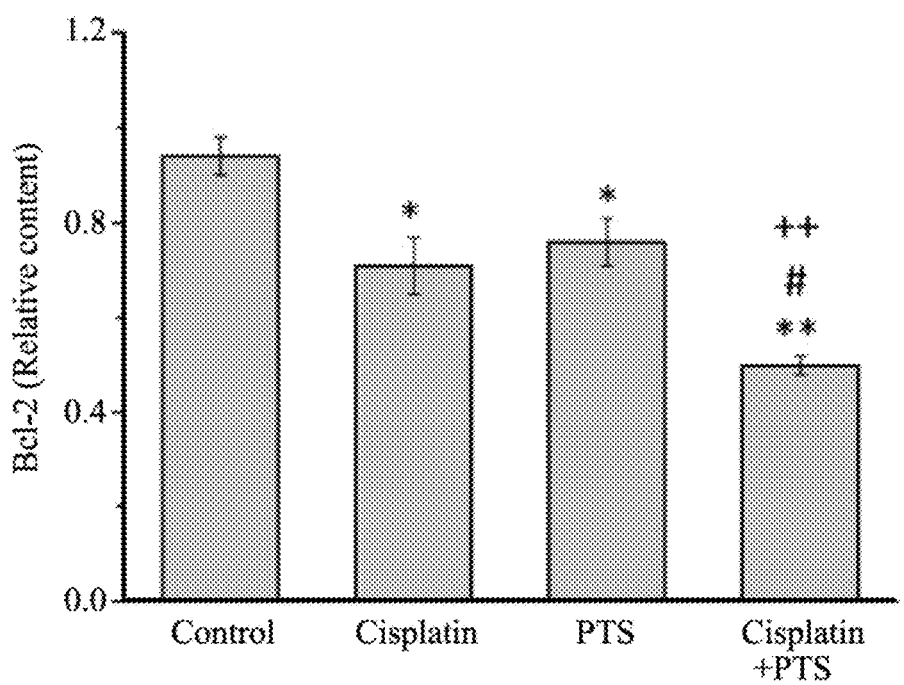

In the present disclosure, during the process of apoptosis, specific enzymes are activated, which dissolve the nuclear components of the apoptotic cells, including the protein components of both the nucleus and the cytoplasm. To further assess the effects of treatments on apoptosis, several proteins with related functions were analyzed as shown in FIG. 3A: anti-apoptosis protein B-cell lymphoma 2 (Bcl-2), extracellular signal-regulated kinase (ERK), phosphorylated ERK, and cleaved caspase 3. According to the western blotting analysis, FIGS. 3B and 3C show the quantitative comparisons of the expression of that cleaved caspase 3 and phosphorylated ERK expression was significantly higher in the cisplatin and PTS (p<0.01 for all) and cisplatin+PTS (p<0.001 for both) groups than in the control group. The combination-treatment group also had higher expression of these proteins than both of the individual-treatment groups (p<0.01 for all except phosphorylated ERK in the cisplatin group, for which p<0.05). As shown in FIG. 3D, expression of Bcl-2, which is thought to suppress apoptosis, was lower in the individual-treatment groups (p<0.05) and the combination-treatment group (p<0.01) than in the control group. There was no significant difference in Bcl-2 expression between the PTS and cisplatin groups, but expression in the cisplatin+PTS group was significantly lower than in both individual-treatment groups (p<0.05 vs PTS, p<0.01 vs cisplatin). Thus, both the PTS and the cisplatin+PTS treatments enhanced the expression of proteins that are associated with the promotion of apoptosis and reduced the expression of a protein that inhibits apoptosis, in which the combination treatment showed the strongest effect.

The production of Cytokines is Restricted by PTS Administration

Figure 4A:
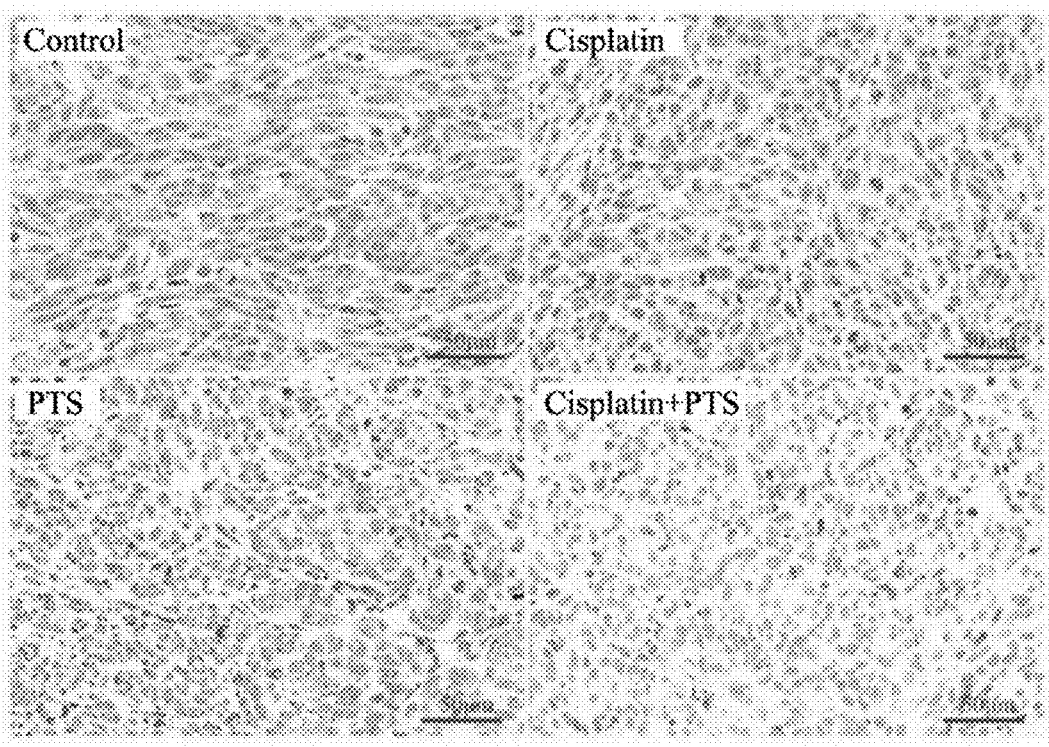
FIGS. 4A to 4E are immunohistochemical (IHC) analysis of expression of three inflammatory cystokines in M5 canine melanoma tumors implanted in BALB/c nude mice.
Figure 4B:
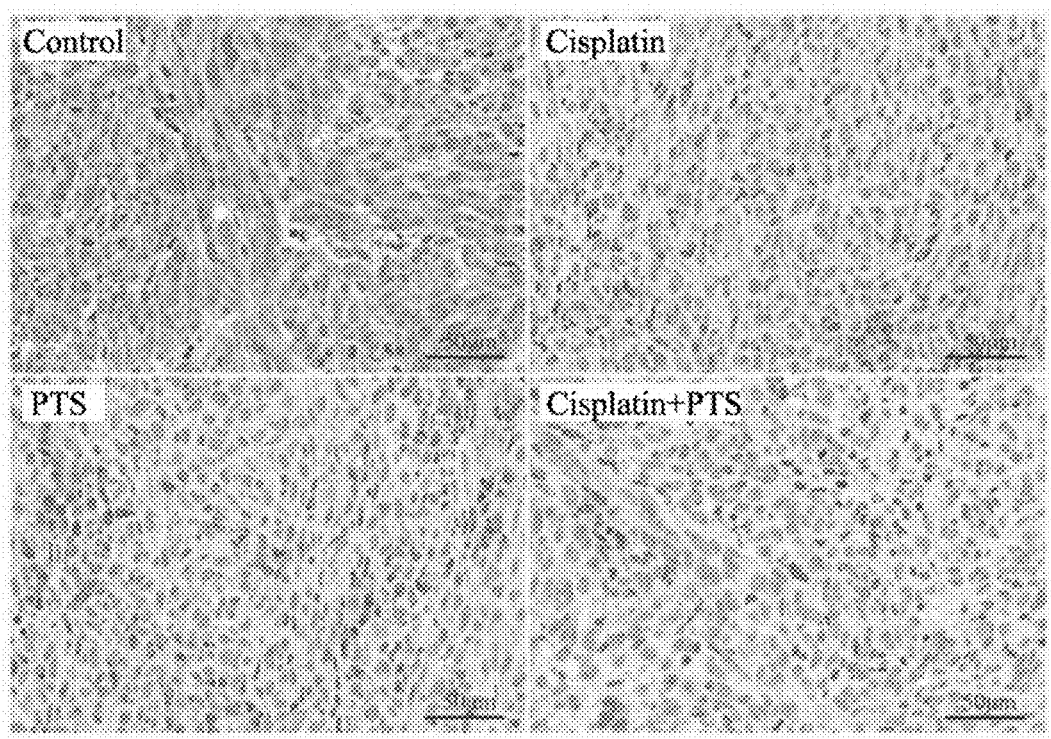
Figure 4C:
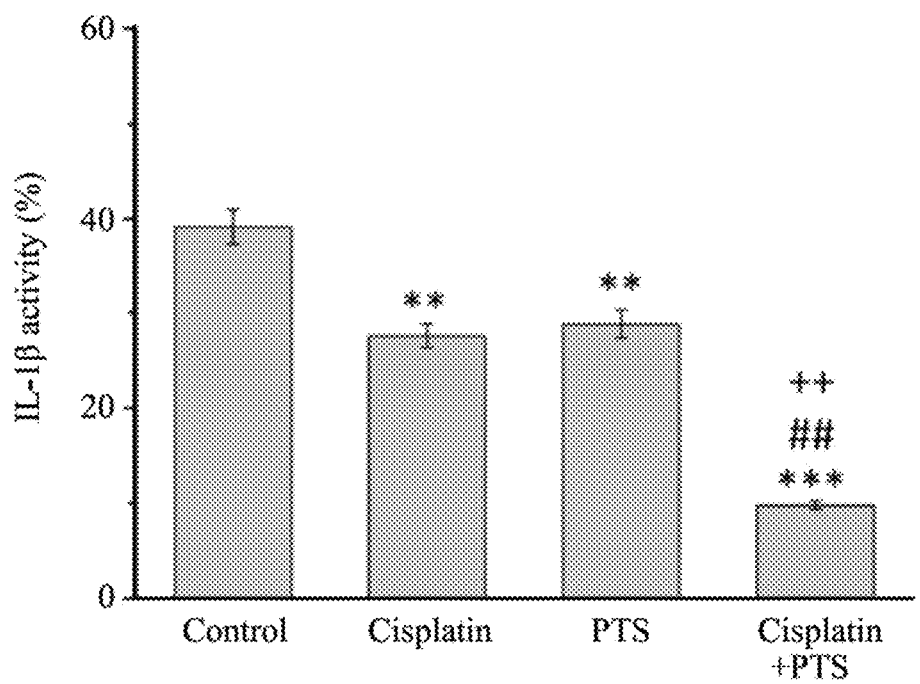
Figure 4D:
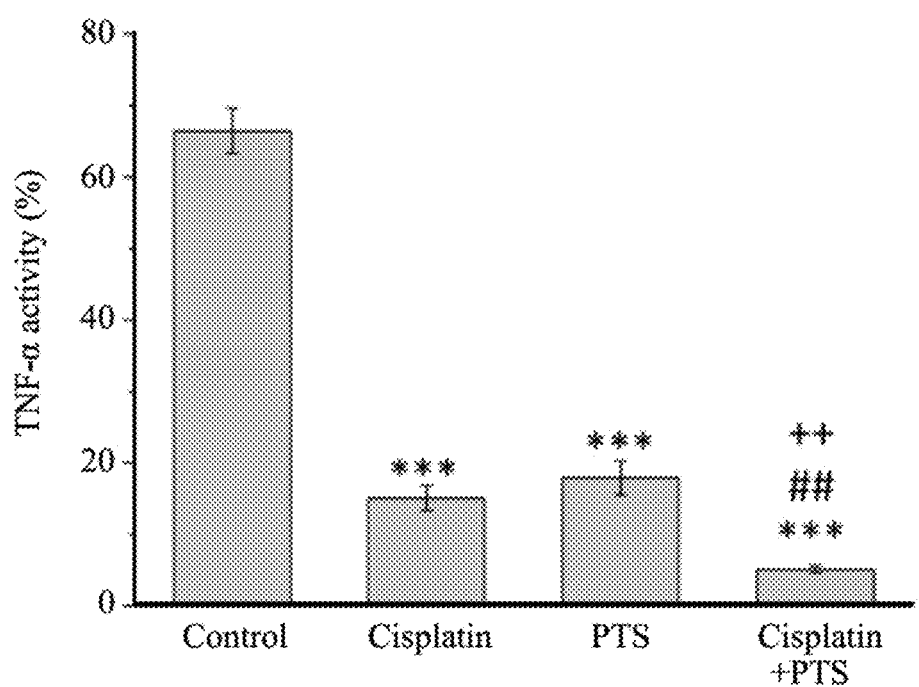

In the present disclosure, there are strong links between inflammation and cancer, and combating inflammation may improve the efficacy of cancer prevention and therapies. One approach of the present disclosure to this is suppressing the expression of inflammatory cytokines. An immune-histochemical (IHC) analysis of the histopathology of the tumors from mice was conducted, focusing on the inflammatory cytokines IL-1β (FIG. 4A) and TNF-α (FIG. 4B). The activity of both was reduced in the cisplatin group by 29.7% and 77.4%, respectively; in the PTS group by 26.5% and 73.0%, respectively; and in the cisplatin+PTS group by 75.0% and 92.2%, respectively, relative to the control group (FIGS. 4C and 4D). There was no significant difference between the PTS and cisplatin groups for either cytokine, and the effect was also strongest in the combination-treatment group. The reduction in the cisplatin+PTS group relative to the PTS group was 65.9% for IL-1β and 71.3% for TNF-α, and relative to the cisplatin group was 64.4% for IL-1β and 65.8% for TNF-α ($p<0.01$ for all). This result demonstrates that the combination treatment was able to strongly suppress the expression of these inflammatory cytokines in canine melanoma.

Figure 4E:
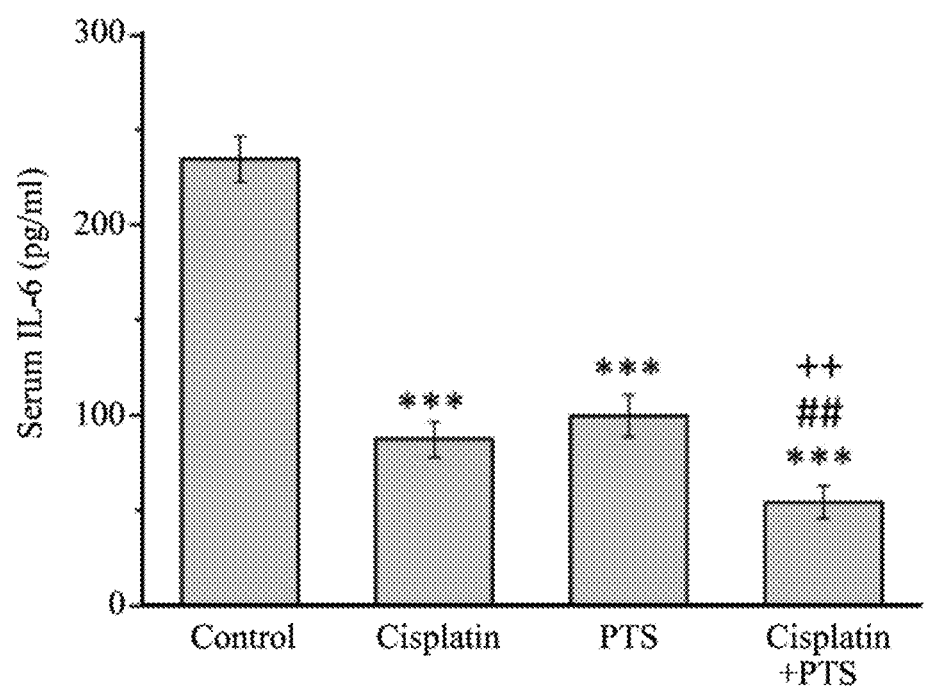

An enzyme-linked immunosorbent assay (ELISA) was conducted to assess the serum expression of IL-6, another inflammatory cytokine. A similar pattern as for IL-1β and TNF-α was observed. Relative to the control group, the expression of IL-6 in the cisplatin, PTS, and cisplatin+PTS groups was reduced by 62.8%, 57.5%, and 76.8%, respectively (FIG. 4E). The present disclosure shows that the difference between the cisplatin and PTS groups was not significant, but the levels in the combination-treatment group were significantly lower than in both the individual-treatment groups (by 37.6% and 45.4%, respectively; $p<0.01$ for both). These findings show that administration of a combination of PTS and cisplatin strongly inhibited the expression of the inflammatory cytokines IL-1β, TNF-α, and IL-6 in cancers, but not limited to, lung squamous cell carcinoma, lung adenocarcinoma and particularly, in canine melanoma.

Figure 5A:
FIGS. 5A to 5D show analysis of factors related to inflammation in M5 canine melanoma tumor implanted in BALB/c nude mice.
Figure 5B:
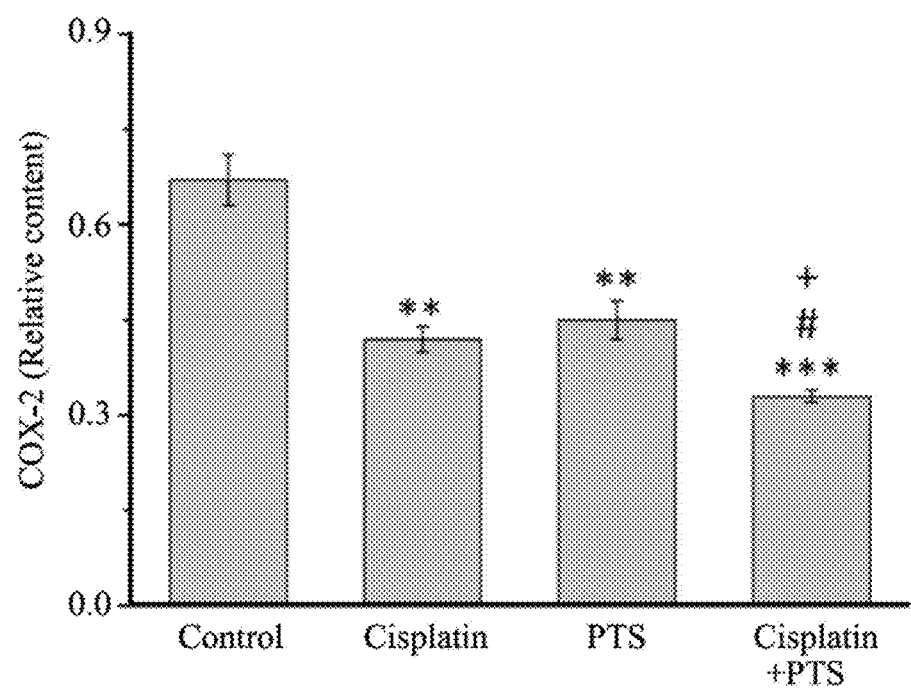

Expression of Inflammation-Related Factors is Reduced in Response to PTS Administration A western blot analysis of factors related to inflammation was conducted. Expression of cyclooxygenase-2 (COX-2) in the cisplatin and PTS groups ($p<0.01$) and the combination-treatment group ($p<0.001$) was lower than that in the control group (FIG. 5A). In at least one embodiment of the present disclosure, the difference between the cisplatin and PTS groups was not significant, but the difference between the combination-treatment group and the cisplatin group or the PTS group was significant ($p<0.05$; FIG. 5B).

Figure 5C:
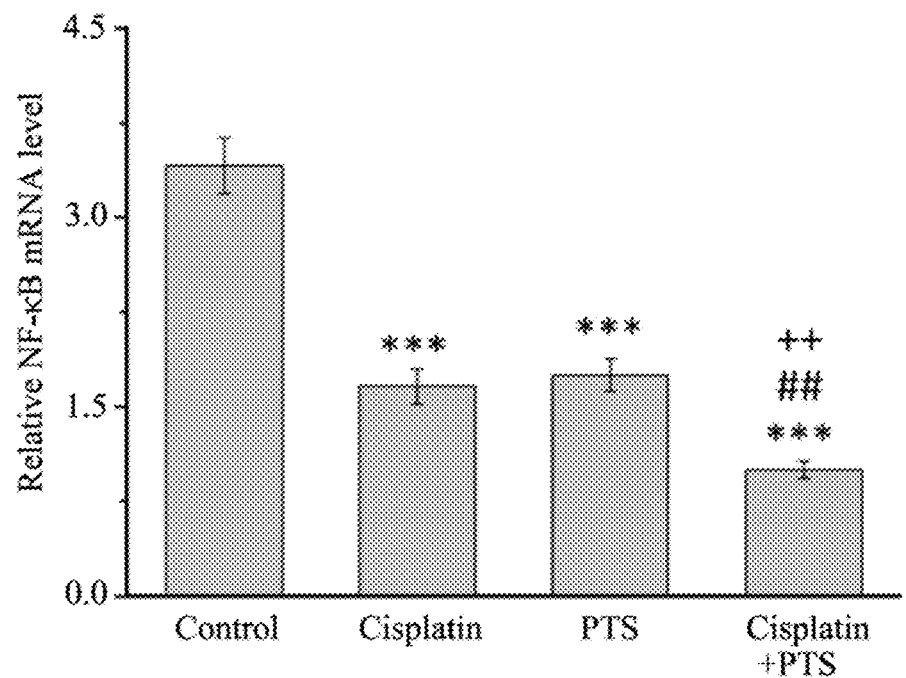
Figure 5D:
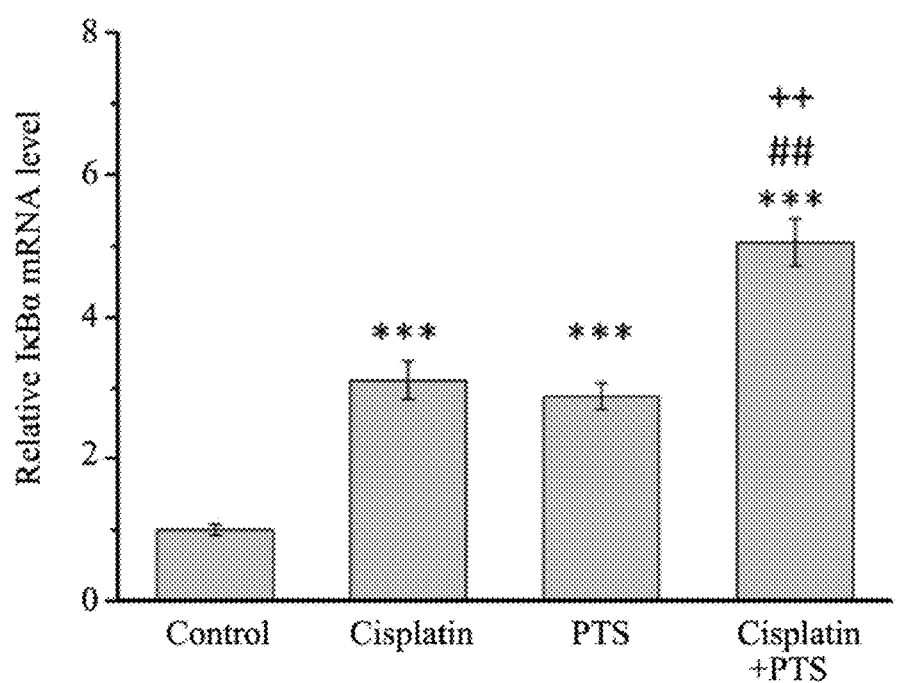

In at least one embodiment of the present disclosure, when cells are stimulated with inflammatory cytokines, IκB kinase (IκBα) degrades, leading to the inhibition of nuclear factor κB (NF-κB), which then accumulates and regulates the expression of specific genes. In the analysis of at least one embodiment of the present disclosure of NF-κB and IκBα mRNA expression, as shown in FIG. 5C, the expression of NF-κB was found to be significantly lower in all three experimental groups ($p<0.001$ for all) than the control group. As expected, the reverse was for IκBα expression ($p<0.001$ for all three experimental groups vs control; FIG. 5D). For both genes, there was no significant difference between the two individual-treatment groups, but the differences between the combination-treatment group and the cisplatin group or the PTS group was significant ($p<0.01$; FIGS. 5C and 5D). These findings indicate that PTS inhibited the expression of inflammation-related factors and responses, although this effect was not different to that of cisplatin. When the two antitumor agents (for instance, Cisplatin+PTS) were combined, the inhibition of the animals' inflammatory response was stronger than the two were not combined.

Factors Related to Metastasis are Reduced by PTS Administration

Figure 6A:
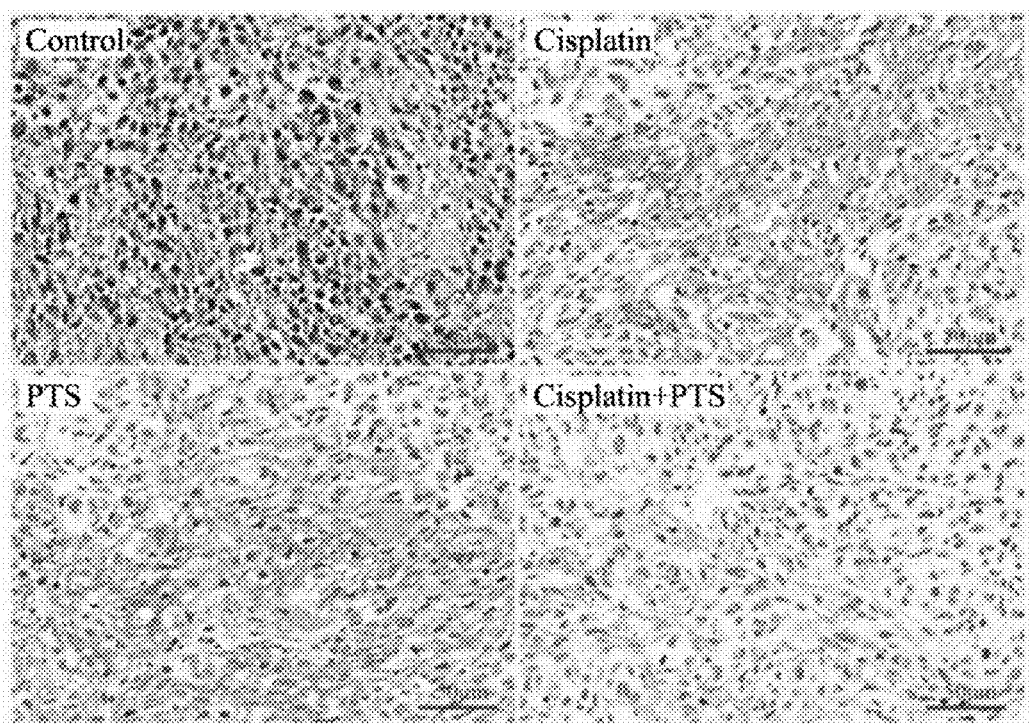
FIGS. 6A to 6G show analysis factors related to metastasis in M5 canine melanoma tumors implanted in BALB/c nude mice. A set of color representative images (FIGS. 6A and 6C) and quantitative comparisons (FIGS. 6B and 6D) from IHC analysis of CD 44 (FIGS. 6A and 6B) and TGF-β (FIGS. 6C and 6D).
Figure 6B:
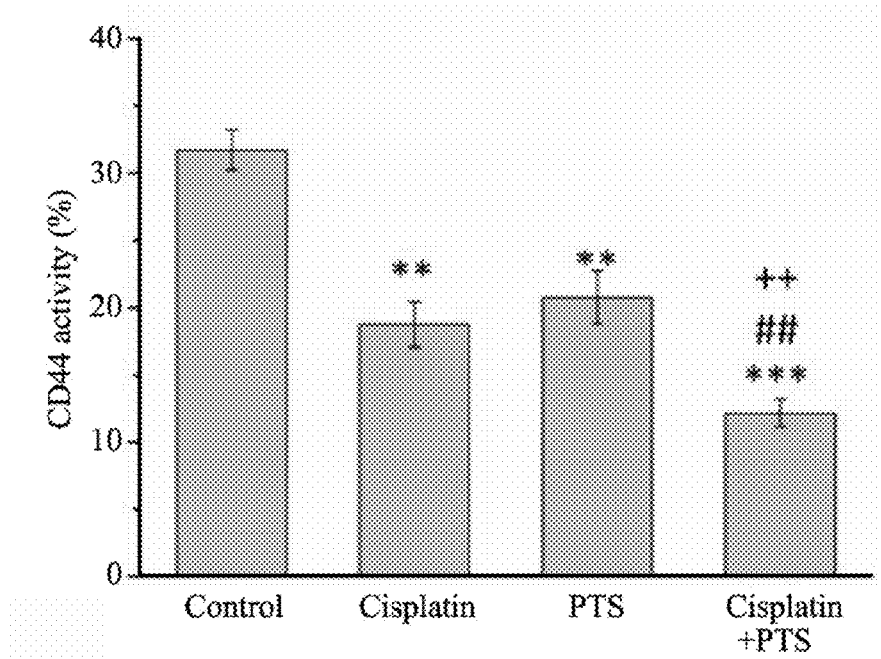
Figure 6C:
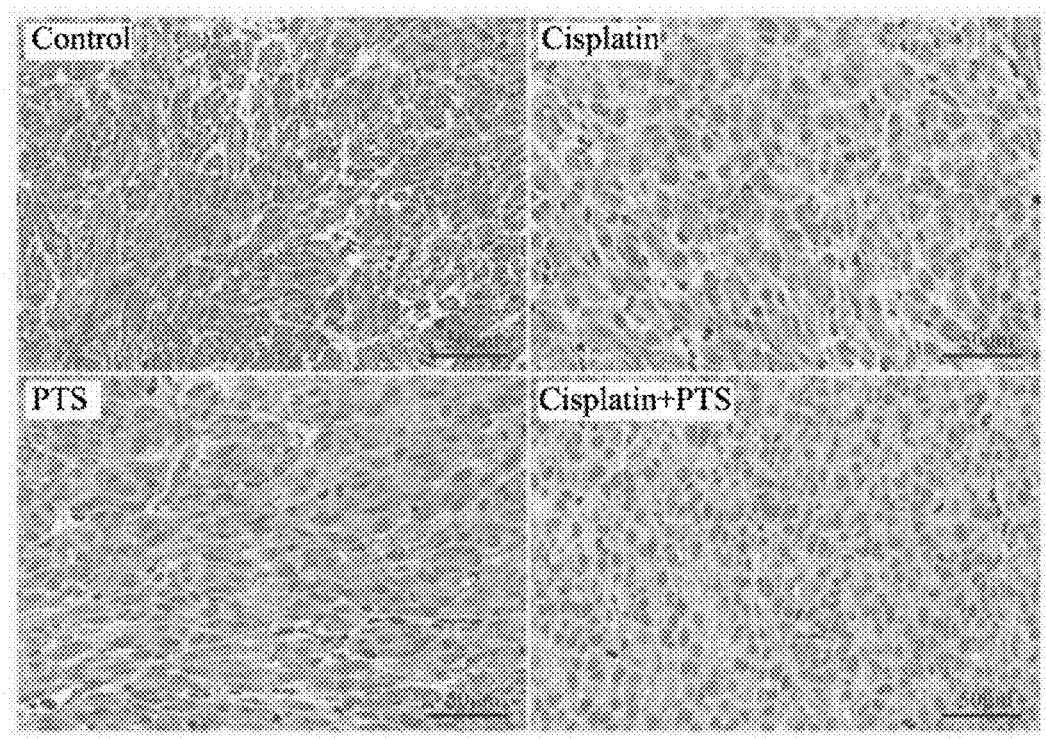
Figure 6D:
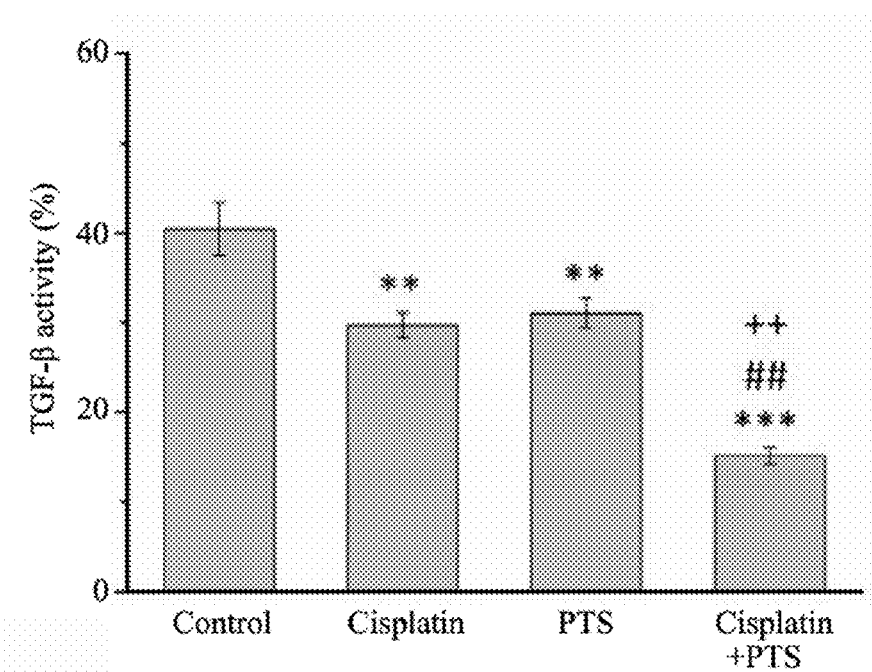
Figure 6E:
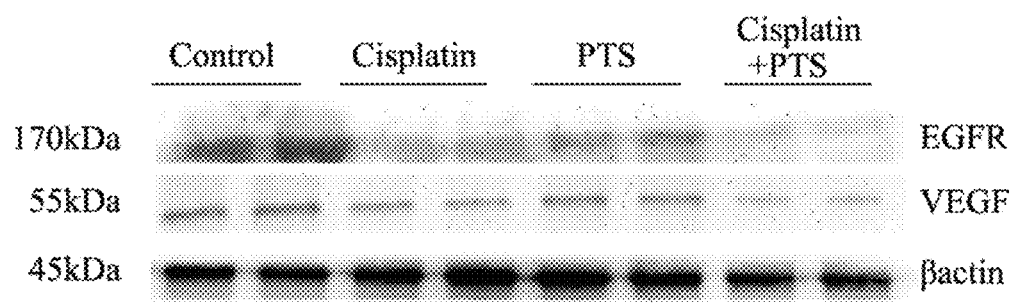

In at least one embodiment of the present disclosure, the high morbidity and mortality associated with cancer, is mainly metastasis. Thus, the expression of TGF-β, CD44, EGFR, and VEGF, were analyzed in the disclosure all of which are related to metastasis. As shown in FIGS. 6A and 6C, TGF-β and CD44 expression were analyzed via IHC and EGFR and VEGF were detected via western blotting, as shown in FIG. 6E. As shown in FIGS. 6B and 6D, the expression of both TGF-β and CD44 was reduced in the cisplatin and PTS groups ($p<0.01$ for all) and in the cisplatin+PTS group ($p<0.001$ for both) relative to the control group. As shown in FIG. 6D, the TGF-β expression in the cisplatin, PTS, and cisplatin+PTS groups was reduced by about 26.6%, 23.3%, and 62.6%, respectively, relative to the control group. Similarly, as shown in FIG. 6B, the CD44 expression was reduced by about 40.9%, 34.4%, and 61.6%, respectively. The difference between the cisplatin and PTS groups was not significant, but significant differences were present between the combination-treatment group and the cisplatin group or the PTS group ($p<0.01$ for all): expression in the cisplatin+PTS group was reduced by 49.0% and 51.2% (TGF-β) and 35.1% and 41.5% (CD44) relative to the cisplatin and PTS groups, respectively.

Figure 6F:
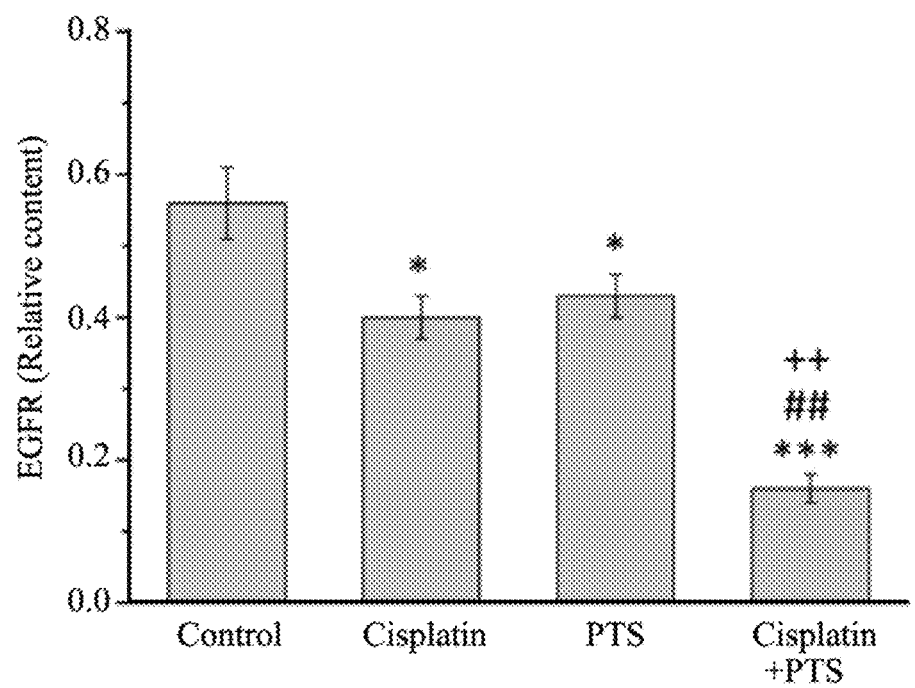
Figure 6G:
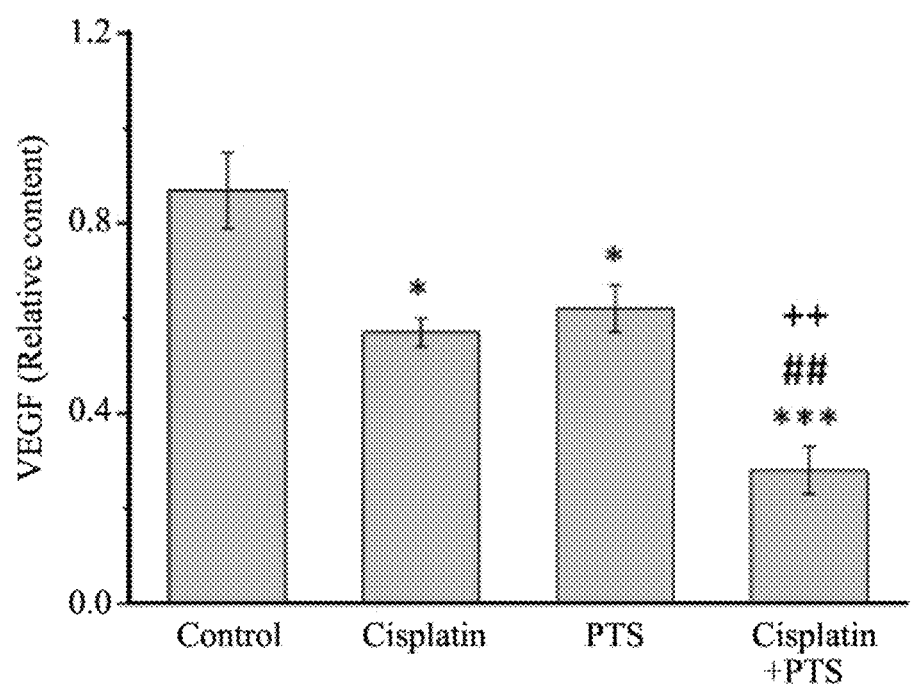

As shown in FIG. 6E, the representative western blot from the analysis of the relative expression of EGFR, the patterns for VEGF and EGFR were similar. As shown in FIGS. 6F and 6G, the expression of both factors was significantly lower in the individual-treatment groups ($p<0.05$ for all) and the combination-treatment group ($p<0.001$ for both) than in the control group. While the relative contents of the EGFR and VEGF in PTS and cisplatin groups are similar, the relative contents of the EGFR and VEGF expression in the cisplatin+PTS combination group was significantly lower than in the other two treatment groups ($p<0.01$ for all). This shows that PTS treatment was able to inhibit the expression of these factors related to metastasis, and that combining PTS with cisplatin or an addition of cisplatin to PTS or an addition of PTS to cisplatin augmented this effect.

In at least one embodiment of the present disclosure, the effects on M5 canine melanoma tumors implanted in nude mice of treatment with PTS alone and in combination with cisplatin. For example, mice have been used as an effective model for assessing the efficacy of treatments on ectopically xenotransplanted human carcinoma cells. Tumor growth may be particularly favorable in such mice because the absence or defective of the thymus which in turn lead to completely or partially lacking of T cells. A similarly effect is observed in uses of cisplatin in treating tumor, just like PTS treatment, both cisplatin and PTS exhibit an effect in reducing tumor size and weight. Even though the effects of PTS and cisplatin are similar when treating tumor, for example, in reducing tumor size and weight, PTS and cisplatin achieved a substantially stronger antitumor effect when they are used in combination, for instances, adding PTS to cisplatin, or adding cisplatin to PTS as a combination therapy. That is, in at least one embodiment of the present disclosure, combination treatment promotes apoptosis by elevating the expression of cleaved caspase 3 and phosphorylated ERK and suppressing that of Bcl-2. Further, combination treatment reduces inflammation by restricting the production of IL-1β, TNF-α, IL-6, COX-2, and NF-κB. Finally, combination treatment renders metastasis less likely by suppressing TGFβ, CD44, VEGF, and EGFR.

In at least one embodiment of the present disclosure, the mTOR pathway is critical for regulating the cell cycle: the mTOR pathway is an important downstream signaling pathway that is activated by many biological functions, and mTOR pathway plays a major role in regulating autophagy. When this mTOR pathway is aberrantly activated, it produces signals that both promote tumor-cell growth and metastasis and enable these cells to invade healthy tissues. In at least one embodiment of the present disclosure, AKT and mTOR, as well as their downstream product p70S6K, are present and active in canine melanoma cells. In at least one embodiment of the present disclosure, activation of the mTOR pathway can be inhibited by rapamycin; treatment of melanoma cells with rapamycin decreased the surviving tumor cell fraction. In at least one embodiment of the present disclosure, inhibiting the mTOR pathway is an effective approach to treating cancer. In at least one embodiment of the present disclosure, the proliferation of M5 canine melanoma is restricted by PTS may be useful in a clinical setting.

In at least one embodiment of the present disclosure, chemotherapy using a combination of an anticancer drug and a cell-signal inhibitor is more effective than single anticancer or antitumor agent. For example, the two active ingredients or drug of the present disclosure can be used in combination with other drugs for treating cancer, such as rapamycin and sorafenib (a multi-kinase inhibitor that inhibits Raf-1 and B-RAF) which the combination of the drugs synergistically reduces melanoma cell proliferation, and these two types of signaling pathway simultaneously may be more effective for treating melanoma than using either agent alone. Drug combinations in canine melanoma treatment were carried out. The MEK inhibitor trametinib and dual PI3K/mTOR inhibitor dactolisib combination synergistically decreased cell survival in association with caspase 3/7 activation, and altered expression of cell cycle regulatory proteins and Bcl-2 family proteins. The inhibitory and synergistic effects of combining cisplatin with PTS to treat mice implanted with M5 canine melanoma cells were assessed. As expected, while PTS alone exhibited inhibitory effects, the combination strongly and synergistically inhibited tumor-cell growth.

Figure 7A:
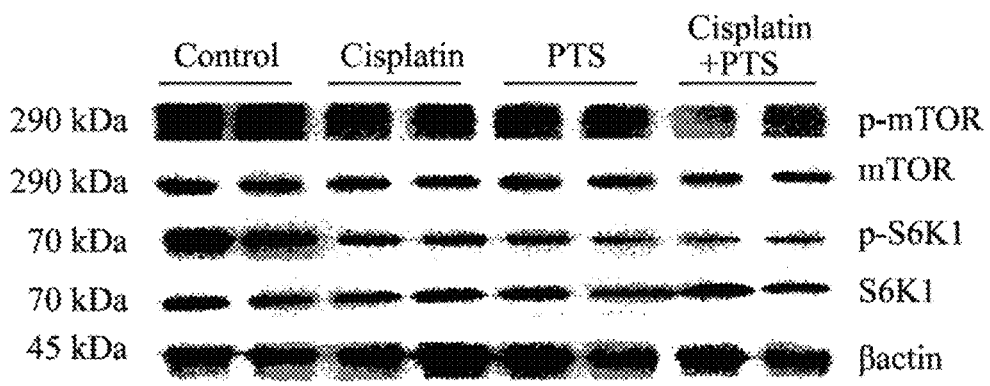
FIGS. 7A to 7C are western blot analysis of aspects of the mTOR signaling pathway in M5 canine melanoma tumors implanted in BALB/C nude mice.
Figure 7B:
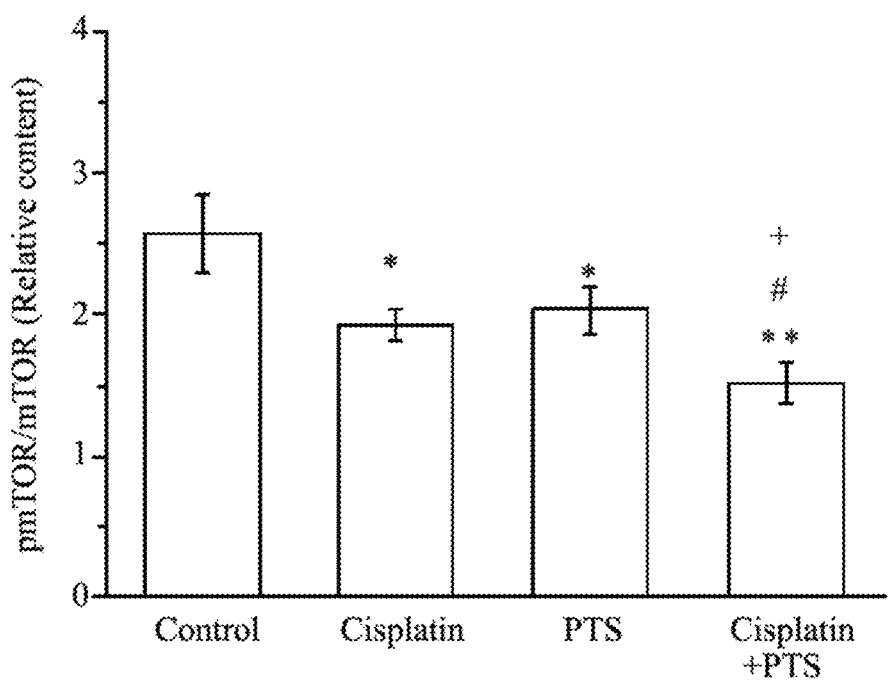
Figure 7C:
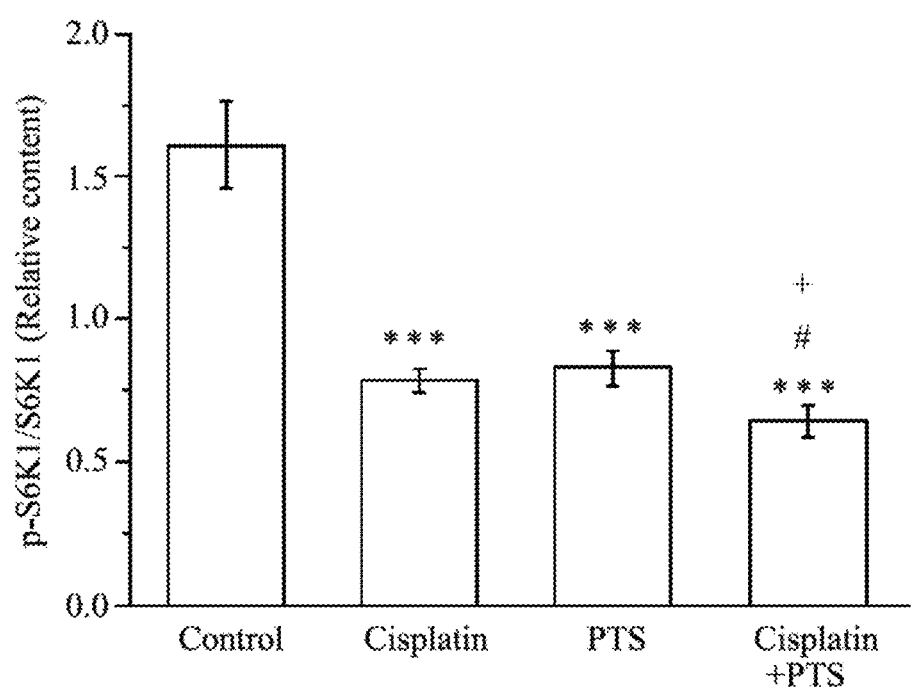

Factors related to apoptosis were examined. This is an important aspect of tumors because cancer cells are able to evade apoptosis despite having abnormalities, and replicate themselves continuously. To further explore the chemotherapeutic approaches force the tumor cells to undergo apoptosis by causing cellular distress or DNA damage that triggers cell-death sig-nals, TUNEL and DAPI assays was conducted to investigate the extent to which apoptosis was occurring in the tumor cells in the mice. As with tumor growth, PTS on its own was beneficial in that it enhanced the tumor-cell apoptosis. However, in combination with cisplatin, treatment strongly promoted apoptosis. This latter treatment therefore reduced the tumor cells' ability to evade apoptosis, thereby limiting tumor growth. Higher expression of cleaved caspase 3 and phosphorylated ERK, both of which are key for apoptosis, in mice administered the combination treatment were observed. The anti-apoptotic Bcl-2 contributes to cancer formation and progression by promoting the survival of altered cells is unexpected. In one embodiment according to the present disclosure, siRNA directed against the canine Bcl-2 gene reduced Bcl-2 mRNA and protein expression in a canine malignant oral melanoma cell line (MCM-N1), and resulted in both a decrease in the number of viable cells and an increase in the apoptotic cell rate. These findings indicate the important role of Bcl-2 activity in inhibition of apoptosis in canine melanoma cells, and reinforce the notion of Bcl-2 as a putative therapeutic target in tumors. In another embodiment according to the present disclosure, rPTS causes the expression of S6K1 and mTOR to be downregulated (FIG. 7A). In at least one embodiment of the present disclosure, PTS must be able to suppress the expression of mTOR, otherwise, the mTOR signaling pathway regulates autophagy and tumor-cell apoptosis may promote tumor occurrence and progression. Accordingly, PTS alone and combined with cisplatin caused the expression of cleaved caspase 3 and phosphorylated ERK to increase significantly relative to the control group. This was probably caused by inhibition of the mTOR pathway. The apoptosis was as expected in corresponding to patterns in tumor size.

Figure 8:
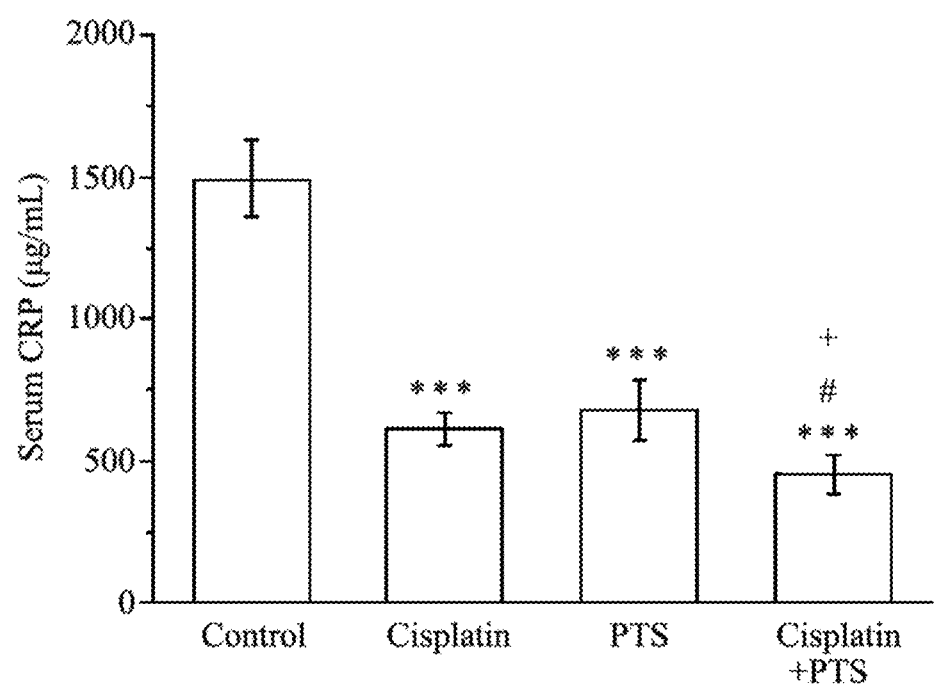
FIG. 8 is bar graph shows serum levels of CRP in BALB/cByJNarl mice implanted with canine melanoma tumor cells. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. ***$p<0.001$ vs control; #$p<0.05$ vs cisplatin; +$p<0.05$ vs PTS.

In another embodiment according to the present disclosure, the effects of PST treatment on various factors relate to inflammation (IL-1β, TNF-α, IL-6, COX-2, NF-κB, and IκBa). The administration of PTS reduces, partially or completely suppresses, the expression of IL-1β, TNF-α, IL-6, COX-2 and NF-κB and the expression of IκBα. Further, CRP is synthesized mainly as a result of stimulation by proinflammatory cytokines, and higher lung-cancer risk and tumor progression are associated with elevated CRP levels. Thus, as shown in FIG. 8, the level of CRP in the serum in mice was lowest when by using PTS and cisplatin in combination.

Figure 9A:
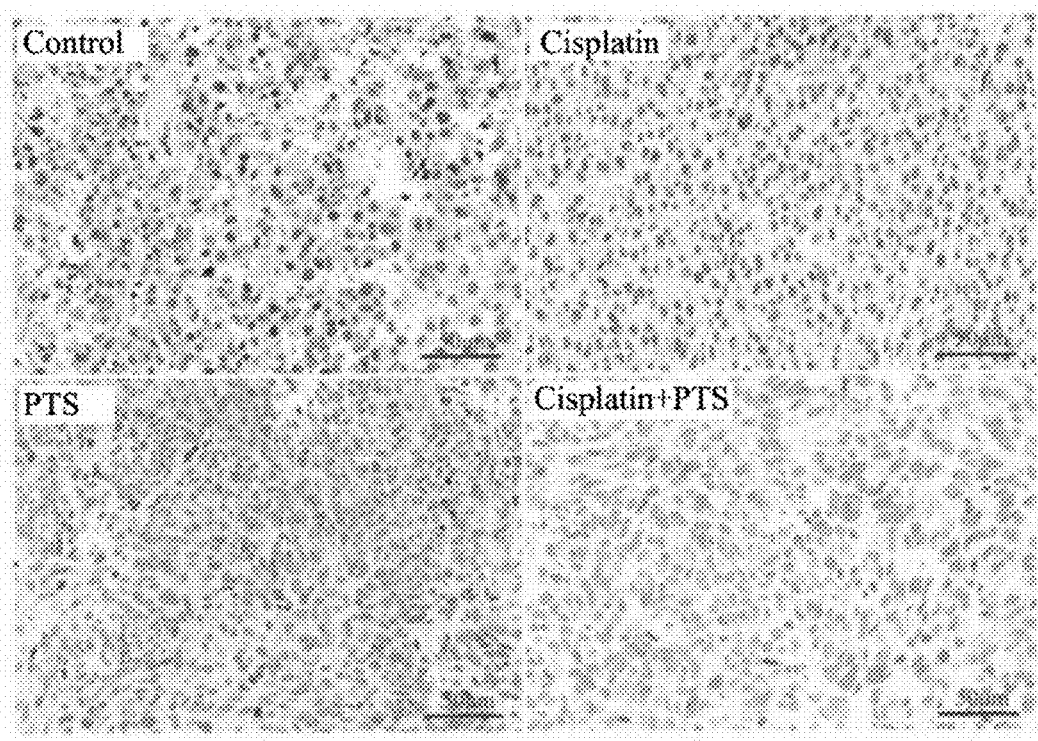
FIGS. 9A to 9B show IHC analysis of Ki67 expression in M5 canine melanoma tumor implanted in BALB/c nude mice.
Figure 9B:
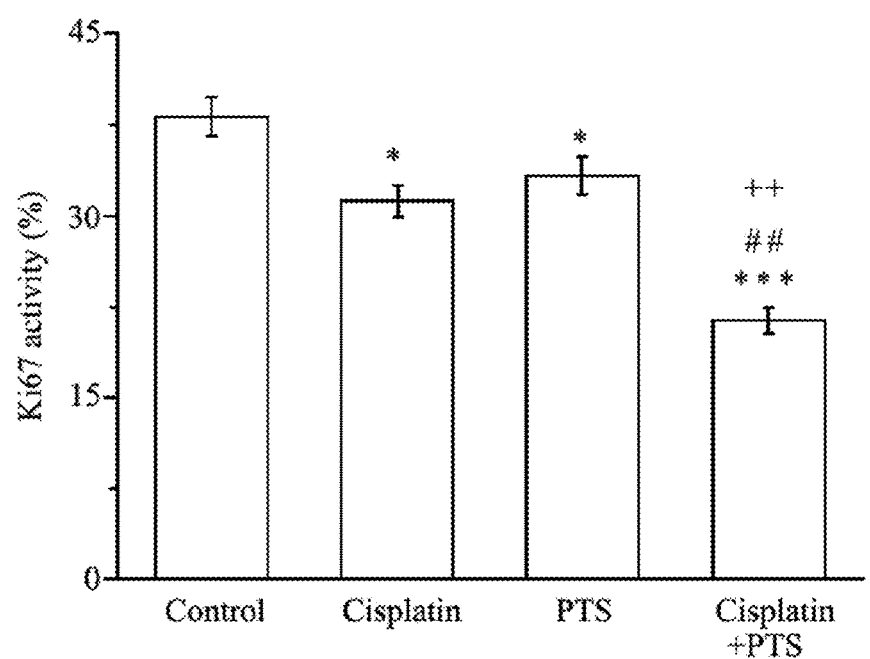

In at least one embodiment of the present disclosure, the combination treatment reduces inflammation by suppressing inflammatory cytokines and promoting anti-inflammation mediators. This is another method in which PTS contributes to retarding tumor growth. In the invention, nuclear protein Ki67 may be a marker for proliferation at inflamed sites and may strongly associated with tumor growth, to the extent that for as an example, canine melanoma, the relative abundance of Ki67-positive tumor cells is used as a prognostic factor. The Ki67 index can be evaluated as differs significantly between malignant and benign melanocytic neoplasms in dogs, and correlates negatively with survival. As shown in FIGS. 9A and 9B, the data has shown that PTS when using alone or in combination with cisplatin has suppressed Ki67 expression. The present data of the invention has demonstrated that PTS can effectively inhibited tumor-growth on the basis of anti-apoptotic factors in at least canine melanoma cells by suppressing inflammation and tumor progression.

Figure 10:
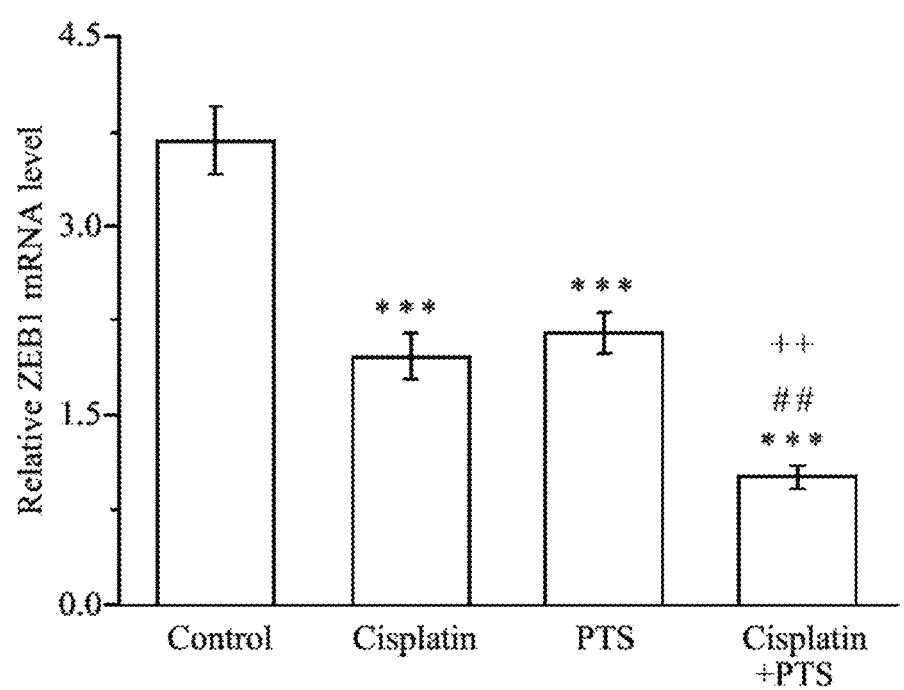
FIG. 10 is a bar graph shows quantitative PCR analysis of the relative expression levels of ZEB1 mRNA in M5 canine melanoma tumors implanted in BALB/c nude mice. The mice were administered the following treatments three times a week (except for the control, which was administered daily): saline (control), 2 mg/kg cisplatin (cisplatin), 100 mg/kg PTS (PTS), or 100 mg/kg PTS and 2 mg/kg cisplatin (cisplatin+PTS). Data are mean±SD, n=7 per group. ***$p<0.001$ vs control; ##$p<0.01$ vs cisplatin; ++$p<0.01$ vs PTS.

In at least one embodiment of the present disclosure, PTS can be used in treating cancer includes means for metastasis reduction. In the examples of the present disclosure, the invFot limited to canine leukemia, melanoma and osteosarcoma and so on. In the present disclosure, PTS, used alone or in combination with cisplatin, substantially suppressed TGF-β and CD44 expression, thereby reducing the metastatic potential of the tumor cells. It is also likely that suppressing TGF-β expression enhances the efficacy of drug therapy by helping to inhibit metastasis. Further, VEGF is another factor in the present disclosure strongly promotes angiogenesis, and overexpression thereof is linked to tumor progression and metastasis. Angiogenesis represents a fundamental step in the malignant growth of tumors and metastasis. Many pro- and anti-angiogenic factors influence the formation of new blood vessels, but the central growth factor in this process is VEGF. Furthermore, VEGF expression appears to be related to tumor grade and prognosis in some malignancies. Over-expression of VEGF in human melanoma results in a phenotype that has increased malignant potential when compared to melanomas with low VEGF expression. EGFR has also shown potential as an important therapeutic target in human cancer, since it may be involved in the progression of cutaneous melanomas specifically, and more generally acts upstream of mTOR as a signal transducer of mitogens that play a role in cancer pathogenesis and development. In addition, expression of zinc finger E-box-binding homeobox 1 (ZEB1), a transcription factor accelerating migration and invasion, indicates epithelial-mesenchymal transition (EMT) in canine melanoma cells. In at least one embodiment of the present disclosure, as shown in FIG. 10, the data has shown that PTS when using alone or in combination with cisplatin has reduced the potential for the M5 canine melanoma cells to metastasize on the basis of the downregulation of ZEB1 mRNA. The present data of the invention has demonstrated that PTS can exert antitumor effects through suppression of VEGF and EGFR expression, especially when administered in combination with cisplatin.

Figure 11A:
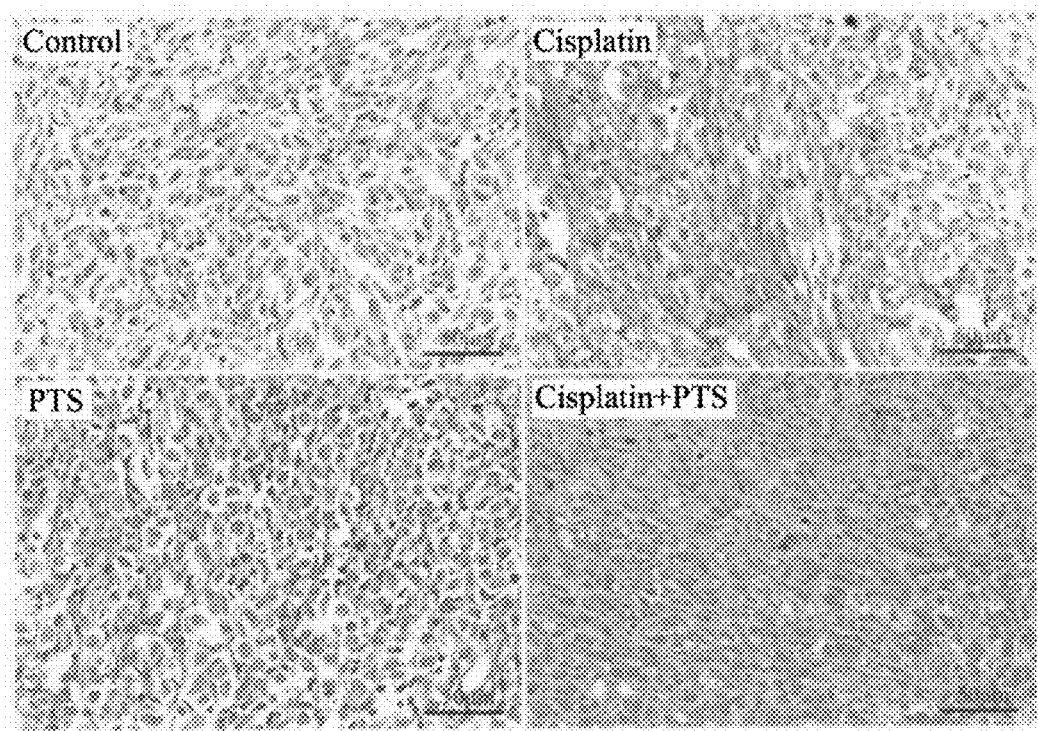
FIGS. 11A to 11B are IHC analysis of CD45 expression in M5 canine melanoma tumors implanted in BALB/c nude mice.
Figure 11B:
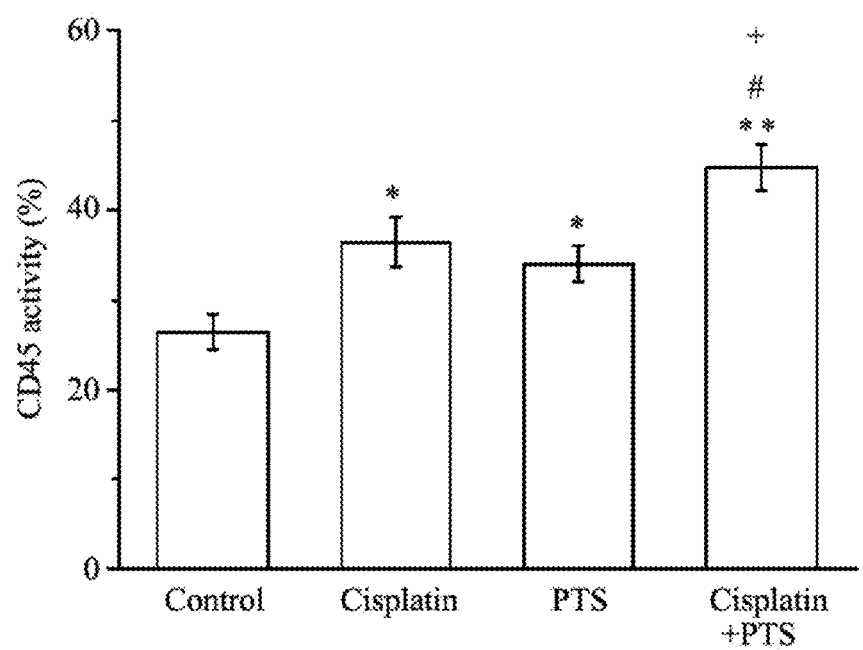

In at least one embodiment of the present disclosure, the tumors of canine and human melanomas are generally resistant to chemotherapy and radiation therapy. Currently, in the area of veterinary oncology, no standard of care for melanoma has been established. In the present disclosure, treatment for dogs with melanoma may include surgery, with the options of hypofractionated or definitive radiation therapy, and platinum chemotherapy. Other therapeutic approaches may include by incorporating carboplatin, cisplatin, and melphalan, but poor response rates and no improvements in survival time have observed. This is particularly the case when chemotherapeutic drugs are tested as the sole treatment or as an adjuvant therapy after surgery or radiation therapy. In an embodiment of the present disclosure, the development and metastasis of tumors are closely related to the tumor microenvironment, which varies in structure and function. The tumor microenvironment may affect tumor progression, prognosis, and the efficacy of immunotherapy, and tumor-infiltrating lymphocytes are reportedly central to these effects. A preferred IHC staining was performed with CD45, a marker for these lymphocytes. As shown in FIGS. 11A and 11B, CD45 activity of the cisplatin, PTS, and cisplatin+PTS groups was 1.4, 1.3, and 1.8 times higher, respectively, than the control group. The present data of the invention has demonstrated that PTS can inhibit cancer, for example, canine melanomas. The inhibition effect was strongest when PTS is used in combination with cisplatin. This combination therapy was determined for strongly inhibiting the growth of M5 cells by promoting apoptosis, suppressing inflammation, and reducing the potential for metastasis.

Experimental Design II

Evaluation of "PTS in Addition to Gemcitabine and Cisplatin" Versus "Gemcitabine and Cisplatin" in Treating Lung Squamous Carcinoma Materials and Methods Male nude-BALB/c mice at six-weeks of age were obtained from National Laboratory Animal Breeding and Research Center, Taipei, Taiwan. Mice were housed in each cage and provided them with sterile food and water. The mice were maintained under a constant temperature (22±2° C.) and relative humidity (55±5%), with a 12:12 h light: dark cycle. The Institutional Animal Care and Use Committee (IACUC) at the National Chiayi University (IACUC Approval No. 110003) reviewed and approved the study protocol, in which procedures were in accordance with the Guidelines for the Care and Use of Laboratory Animals published by the Taiwanese Ministry of Health and Welfare.

Inoculation and Treatment of Tumors

Human non-small cell lung carcinoma cell line (H520) was purchased from ATCC Cell Bank. H520 cells were incubated in RPMI 1640 medium (cat no. 61870044; Gibco; Thermo Fisher, Inc) supplemented with 10% fetal bovine serum in an environmental containing 5% $CO_2$ at 37° C. The experimental treatments were commenced after the implanted H520 cells had formed a detectable tumor mass, which was assessed on day 7 after implantation. Briefly, the mice were anesthetized via intraperitoneal injection of Zoletil (Virbac Taiwan, Taipei, Taiwan), and then subcutaneously injected 100 µl of cell suspension containing $5*10^6$ viable H520 cells into right posterior leg. The development of the tumor lesions was assessed on day 7, and randomly divided the animals that showed a start dosage tumor volume of 100 mm³ into four groups (10 mice per group). All treatments were administered via intraperitoneal injection (IP) or intratumoral injection (IT). The control group (Group 1) received normal saline daily, while the other three treatment groups received their corresponding treatments B.I.W (twice a week) or Q.W (once weekly). The PTS100 group (Group 2) received 330 mg/kg of PTS100 (Gongwin Biopharm Holding, Taipei, Taiwan). The Gemcitabine+Cisplatin group (Group 3) received 160 mg/kg of gemcitabine and 3 mg/kg of cisplatin. The Gemcitabine+cisplatin+PTS100 (Group 4) received 160 mg/kg of gemcitabine, 3 mg/kg of cisplatin, and 300 mg/kg of PTS 100. In group 4, when administering in combination, gemcitabine+cisplatin and PTS are given at different days, for example, PTS is given at Monday and Thursday, and gemcitabine+cisplatin is given at Wednesday. See Table 2 for the experimental design of the corresponding treatments, dose, injection site, concentration, volume, number of subjects and dosing frequency. The dosage of cisplatin, gemcitabine, and PTS100 were selected such that these drug affects apoptosis, invasion, metastasis, angiogenesis, and the growth signal mechanisms in canine melanoma implanted in mice. The growth of the tumors was assessed every seven days by measuring their largest and smallest diameters, and calculated their volume according to the following formula: $V=0.5 \times a \times b2$, where a and b are the largest and smallest diameters, respectively.

TABLE 2

| Group | Treatment | Dose (mg/kg) | Injection | Concentration (mg/mL) | Volume (mL) | N | Dosing Frequency |
|---|---|---|---|---|---|---|---|
| 1 | Normal saline | — | IP | — | BW(g) × 10 uL/g[a] | 10 | B.I.W.[b] |
| 2 | PTS100 | 330 | IT[c] | 330 mg/mL | BW(g) × 1.0 uL/g[d] | 10 | B.I.W. |
| 3 | Gemcitabine | 160 | IP | 16 mg/mL | BW(g) × 10 uL/g | 10 | QW[e] |
|  | cisplatin | 3 | IP | 300 ug/mL | BW(g) × 10 uL/g |  | QW |
| 4[f] | Gemcitabine | 160 | IP | 16 mg/mL | BW(g) × 10 uL/g | 10 | QW |
|  | cisplatin | 3 | IP | 300 ug/mL | BW(g) × 10 uL/g |  | QW |
|  | PTS100 | 330 | IT | 330 mg/mL | BW(g) × 1.0 uL/g |  | B.I.W. |

[a]volume is calculated based on 20 g of the mice BW, for ex. 20 g × 10 μL/g = 200 μL
[b]B.I.W. stands for dosing frequency of twice a week
[c]I.T = intratumoral injection. Total volume is split to 3 different injection sites.
[d]PTS100 has a concentration of 330 mg/ml. For example, when the dosage is at 300 mg/kg, the volume is 20 g (mice BW) × 1 μL/g = 20 μL
[e]QW stands for dosing frequency of once a week
[f]when administering in combination, gemcitabine + cisplatin and PTS are given at different days.

Figure 12A:
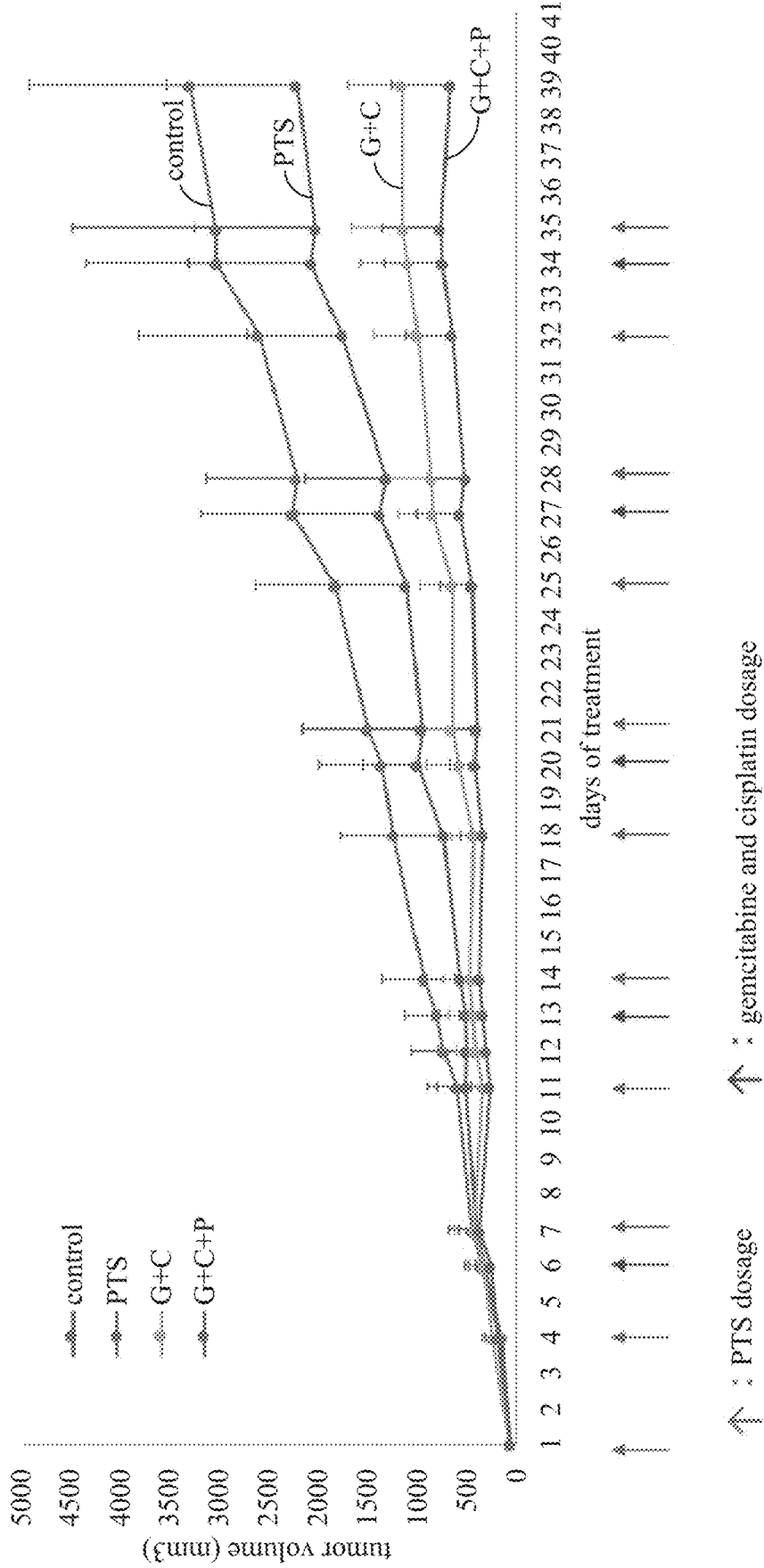
FIGS. 12A to 12C show effects of treatment with PTS combined chemotherapy in lung squamous cell carcinoma in BALB/c nude mice in the first experiment.

Treatment with PTS as a single agent induced a slight decrease in tumor volume compared to control, while addition of Gemcitabine+Cisplatin to PTS resulted in a strong decrease in tumor burden, as shown in FIG. 12A. Importantly, the addition of Gemcitabine+Cisplatin enhanced the antitumor activity of PTS in this model.

This effect was most prominent in the group receiving PTS first followed by gemcitabine and cisplatin, such as day 13 (FIG. 12A). Furthermore, this drug combination was more effective than single agent PTS at reducing tumor burden in large tumors. In day 13 of the anti-tumor therapy, the tumor volume resulted in a significant increase in the control group, while the tumor volume in Groups 2, 3, and 4 remains constant at a low tumor volume. After about 32 days of treatment, the tumor volume of control was well over 2500 cm$^3$, while group 3 and 4 shows significant enhanced antitumor activity. As shown in Table 3, the tumor growth inhibition in group control were 0%, in the PTS was 39.2%, in G+C group was 60.1% and in G+C+P group was 80%. Compared with control, G+C+P shows significant enhanced antitumor activity for lung squamous lung carcinoma.

TABLE 3

| group | inhibition |
|---|---|
| control | 0.0% |
| PTS | 39.2% |
| G + C | 60.1% |
| G + C + P | 80.0% |

Figure 12B:
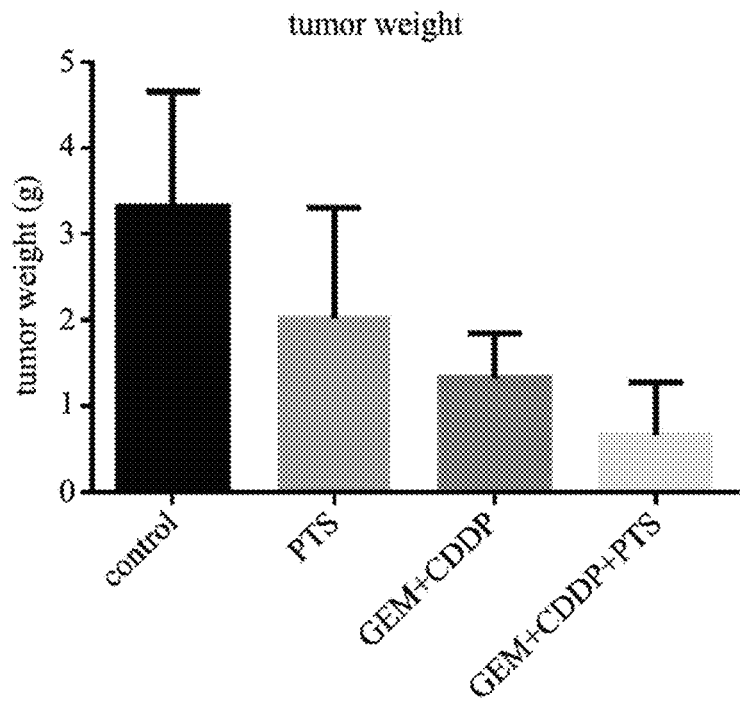
Figure 12C:
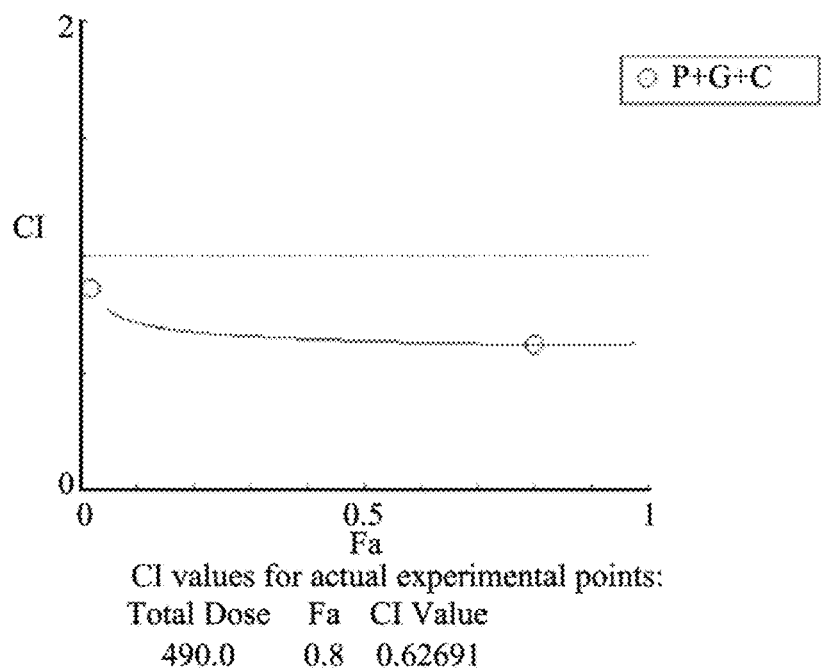

As seen in FIG. 12B, the tumor weight of G+C+P is also the lowest compared to the tumor weight of the control. Table 4 shows the reference of combination index and its description in which the combination index method is based on those described by Chou and Talahay et al (1984) and the computer software of Chou and Martin (2005). The ranges of CI are refined from those described earlier by Chou (1991). In this present disclosure, CI<1, =1, and >1 indicate synergism, additive, and antagonism, respectively. FIG. 12C highlighted both a Fraction affected (Fa) of about 0.80 and a combination index (CI) of about 0.63, which specify, respectively, the synergic effect of such combo G+C+P and this synergism outcome of G+C+P that were able to increase the efficacy of the therapeutic effect for lung squamous lung carcinoma.

TABLE 4

| Description of Combination Index | Description | Graded Symbols |
|---|---|---|
| <0.1 | Very strong | +++++ |
| 0.1-0.3 | Strong synergism | ++++ |
| 0.3-0.7 | Synergism | +++ |
| 0.7-0.85 | Moderate synergism | ++ |
| 0.85-0.90 | Slight synergism | + |
| 0.90-1.10 | Nearly additive | ± |
| 1.10-1.20 | Slight antagonism | – |
| 1.20-1.45 | Moderate antagonism | – – |
| 1.45-3.3 | Antagonism | – – – |
| 3.3-10 | Strong antagonism | – – – – |
| >10 | Very strong antagonism | – – – – – |

Figure 13A:
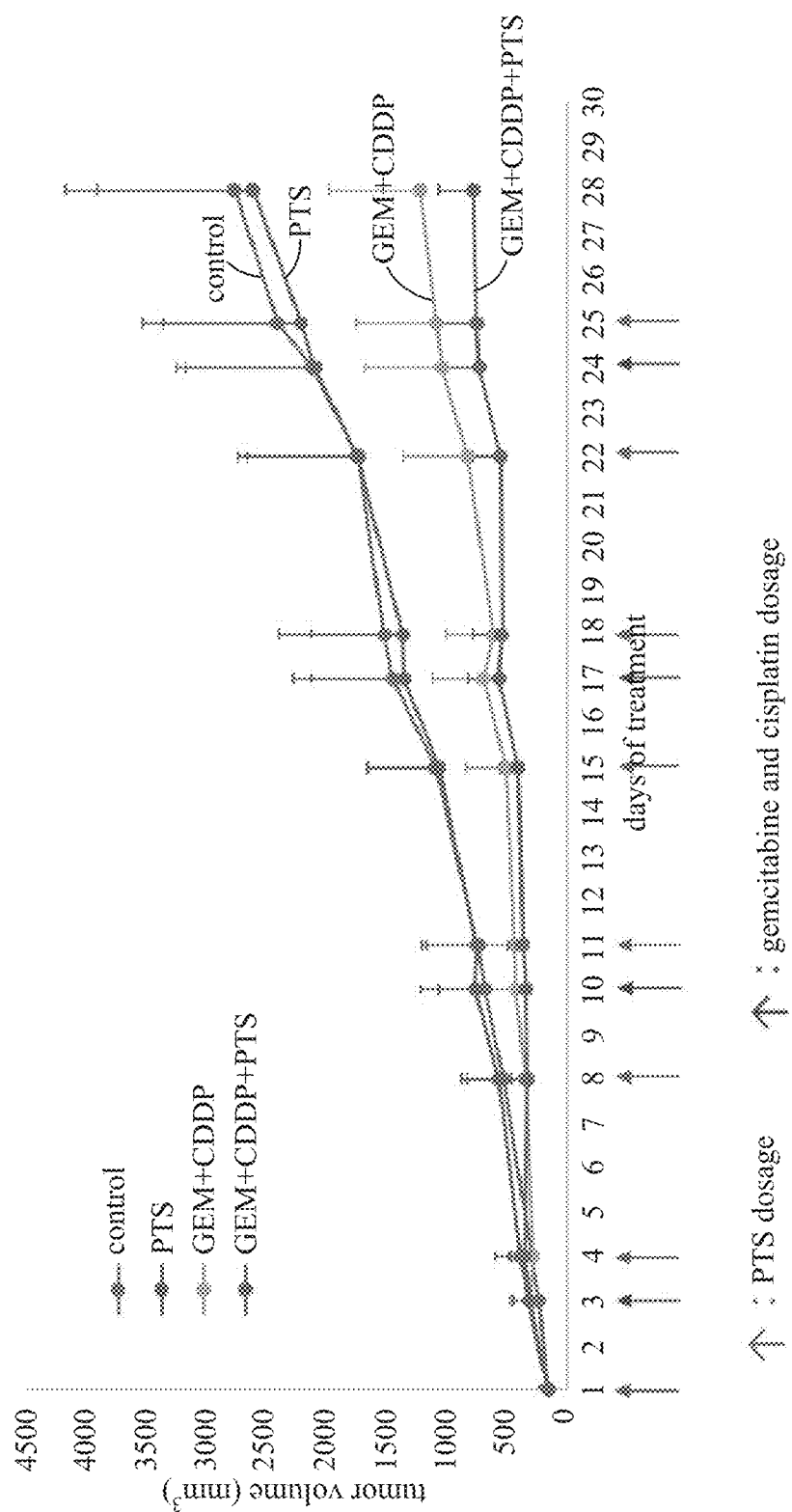
FIGS. 13A to 13C show effects of treatment with PTS combined chemotherapy in lung squamous cell carcinoma in BALB/c nude mice in repeated (second) experiment.
Figure 13B:
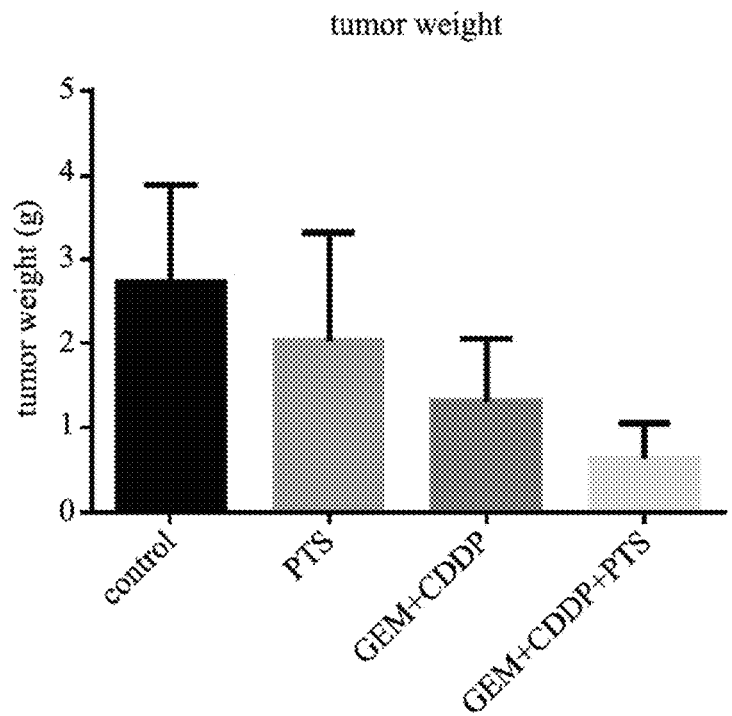
Figure 13C:
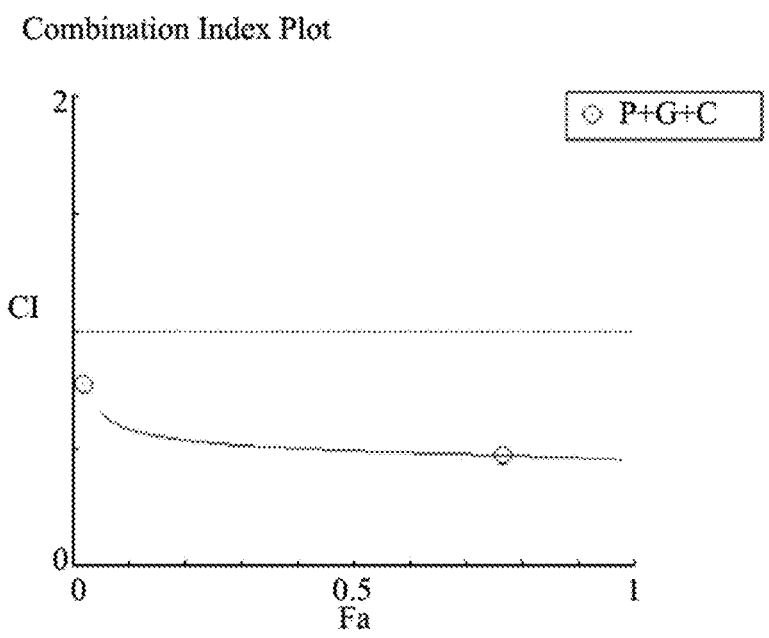

In a repeat experiment, as shown in FIG. 13A, the mice received treatments with PTS as a single agent induced a slight decrease in tumor volume compared to control, while addition of Gemcitabine+Cisplatin to PTS resulted in a strong decrease in tumor burden, as shown in FIG. 13B. Similar results were observed in Groups 3 (G+C) and 4 (G+C+P), in which, the tumor volume resulted in a significant increase in the control, while the tumor volume in Groups 2, 3, and 4 remains constant at a low tumor volume. FIG. 13C highlighted both a Fraction affected (Fa) of about 0.77 and a combination index (CI) of about 0.47, which specify, respectively, the synergic effect of such combo G+C+P and this synergism outcome of G+C+P that were able to increase the efficacy of the therapeutic effect for lung squamous lung carcinoma.

The novel finding that the addition of Gemcitabine+Cisplatin to PTS can decrease the tumor growth rate for lung squamous lung carcinoma is unexpected.

Experimental Design III

Evaluation of Combination Therapy in Treating Lung Adenocarcinoma

Inoculation and Treatment of Tumors

A549 cell line was purchased from ATCC Cell Bank and was cultured in F-12K medium (cat no. ATCC 30-2004) plus 10% fetal bovine serum, at 37° C., 5% CO2. For experiments, cells were grown to 90% confluence. The experimental treatments were commenced after the implanted A549 cells had formed a detectable tumor mass, which was assessed on day 7 after implantation. Briefly, the mice were anesthetized via intraperitoneal injection of Zoletil (Virbac Taiwan, Taipei, Taiwan), and then subcutaneously injected 100 μl of cell suspension containing 6*10$^6$ viable A549 cells into right posterior leg. The development of the tumor lesions was assessed on day 7, and randomly divided the animals that showed a start dosage tumor volume of 100 mm$^3$ into four groups (10 mice per group). All treatments were administered via intraperitoneal injection (IP) or intratumoral injection (IT). The control group (Group 1) received normal saline daily, while the other three treatment groups received their corresponding treatments B.I.W (twice a week) or Q.W (once weekly). The PTS100 group (Group 2) received 330 mg/kg of PTS100 (Gongwin Biopharm Holding, Taipei, Taiwan). The normal saline+pemetrexed+Cisplatin group (Group 3) received 100 mg/kg of pemetrexed and 2 mg/kg of cisplatin. The pemetrexed+cisplatin+PTS100 (Group 4, also known as the "combination") received 100 mg/kg of pemetrexed, 2 mg/kg of cisplatin, and 330 mg/kg of PTS 100. In group 4, when administering in combination, pemetrexed, cisplatin, PTS100 are given at different days, for example, PTS is given at Monday and Thursday, and pemetrexed+cisplatin is given at Wednesday. See Table 4 for the experimental design of the corresponding treatments, dose, injection site, concentration, volume, number of subjects and dosing frequency. The dosage of pemetrexed, cisplatin, and PTS100 were selected such that these drug affects apoptosis, invasion, metastasis, angiogenesis, and the growth signal mechanisms in canine melanoma implanted in mice. The growth of the tumors was assessed every seven days by measuring their largest and smallest diameters, and calculated their volume according to the following formula: V=0.5×a×b2, where a and b are the largest and smallest diameters, respectively.

14A). Furthermore, group 4 was more effective than group 2, that is, the group containing cisplatin and pemetrexed without PTS, at reducing tumor burden in large tumors. After 35 days of the anti-tumor therapy, the tumor volume resulted in a significant increase in the control, while the tumor volume in Groups 2, 3, and 4 remains constant at a low tumor volume. Furthermore, after about 40 days of treatment, the tumor volume of the Control and Group 2 was well over about 1000 and 700 cm$^3$, respectively, while groups 3 and 4 show significant enhanced antitumor activity. As shown in Table 5, the tumor growth inhibition in group control were 0%, in the PTS was 84.13%, in C+P group was 32.60% and in G+C+P group was 95.20%. Compared with control, the groups containing PTS100 show significant enhanced antitumor activity for lung squamous lung carcinoma.

TABLE 5

| group | Inhibition (%) |
| --- | --- |
| control | 0 |
| PTS | 84.13 |
| Cisplatin + Pemetrexed (C + P) | 32.60 |
| PTS + Cisplatin + Pemetrexed (G + C + P) | 95.20 |

Figure 14A:
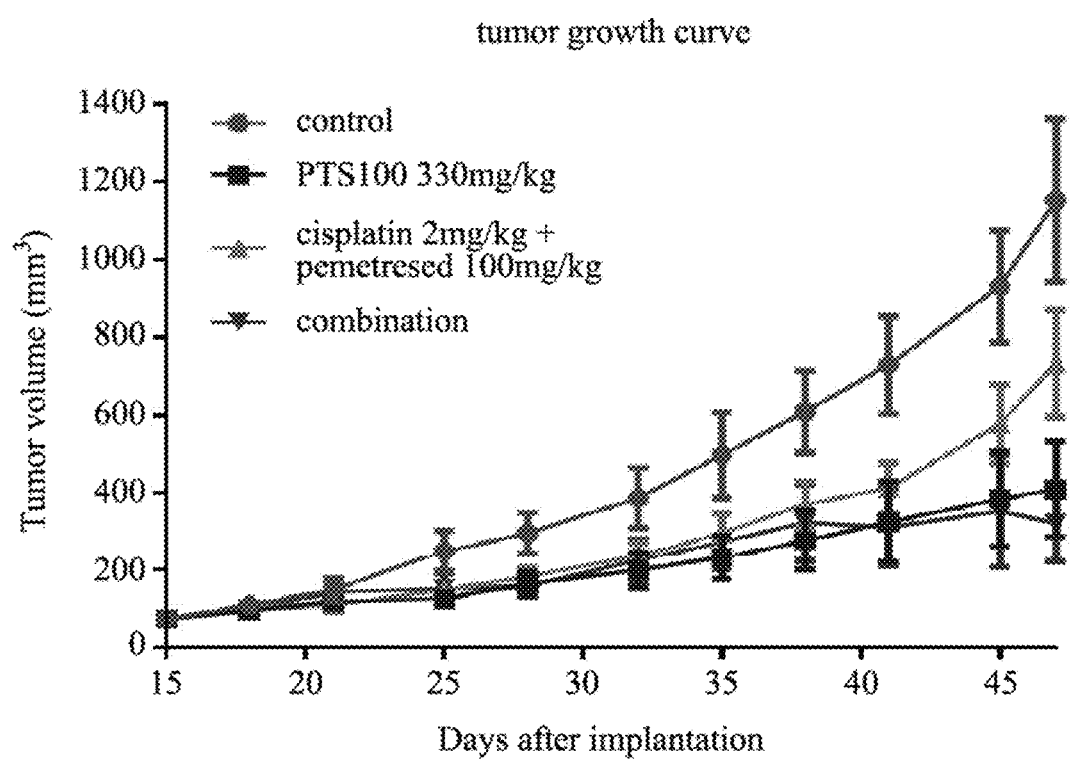
FIGS. 14A to 14C show effects of treatment with PTS combined chemotherapy in lung adenocarcinoma in BALB/c nude mice.
Figure 14B:
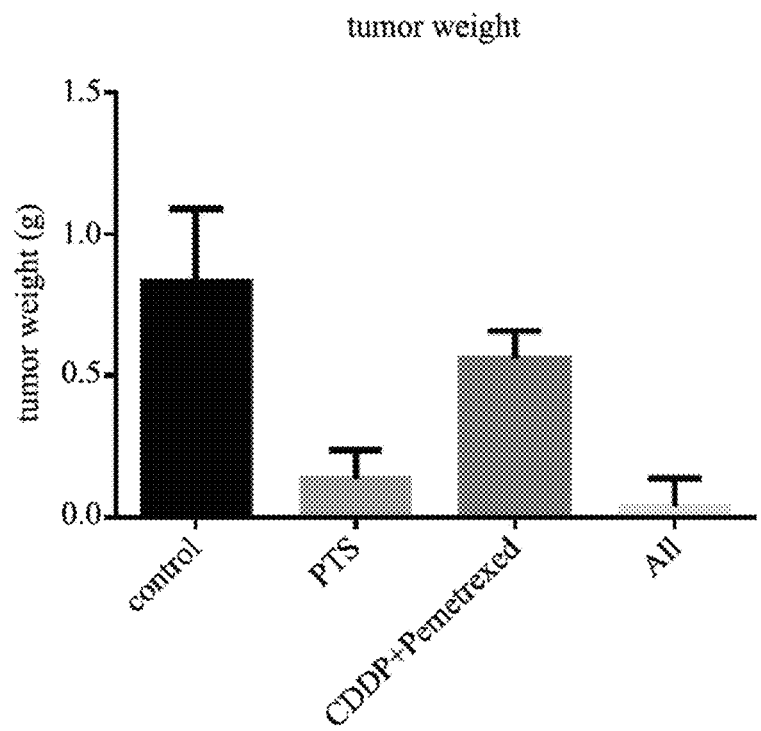
Figure 14C:
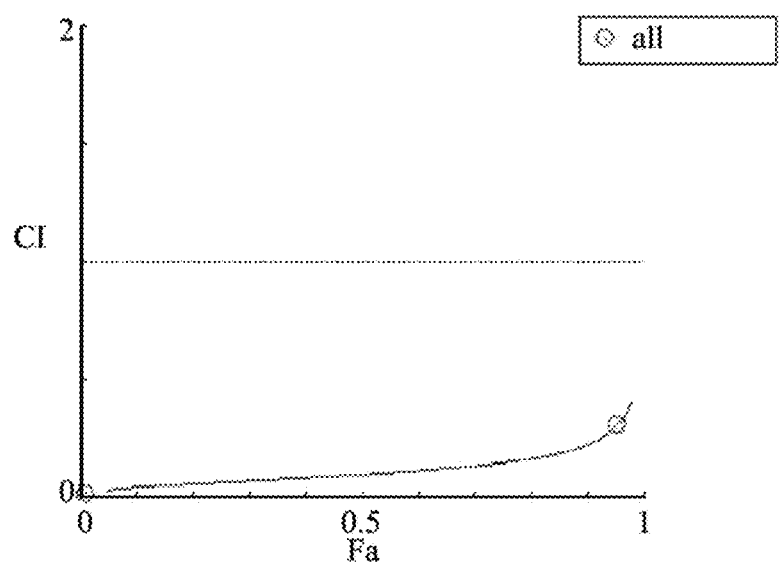

As seen in FIG. 14B, the tumor weight of G+C+P is the lowest compared to the tumor weight of the control. Also, the tumor weight of the PTS group also shows a significant decrease in tumor weight. In this present disclosure, CI<1, =1, and >1 indicate synergism, additive, and antagonism, respectively. FIG. 14C highlighted both a Fraction affected (Fa) of about 0.952 and a combination index (CI) of about 0.31, which specify, respectively, the synergic effect of such combo in group 4 and this synergism outcome of

TABLE 4

| Group | Treatment | Dose (mg/kg) | Injection | Concentration (mg/mL) | Volume (mL) | N | Dosing Frequency |
| --- | --- | --- | --- | --- | --- | --- | --- |
| 1 | Normal saline | — | IT | — | BW(g) × 1.0 uL/g$^a$ | 10 | B.I.W.$^b$ |
| 2 | PTS100 | 330 | IT$^c$ | 330 mg/mL | BW(g) × 1.0 uL/g$^d$ | 10 | B.I.W. |
| 3 | Normal saline | — | IT | — | BW(g) × 1.0 uL/g | 10 | B.I.W. |
|   | pemetrexed | 100 | IP | 25 mg/mL | BW(g) × 4 uL/g |   | QW$^e$ |
|   | cisplatin | 2 | IP | 400 ug/mL | BW(g) × 5 uL/g |   | QW |
| 4$^f$ | pemetrexed | 100 | IP | 25 mg/mL | BW(g) × 4 uL/g | 10 | QW |
|   | cisplatin | 2 | IP | 400 ug/mL | BW(g) × 5 uL/g |   | QW |
|   | PTS100 | 330 | IT | 330 mg/mL | BW(g) × 1.0 uL/g |   | B.I.W. |

$^a$volume is calculated based on 20 g of the mice BW, for ex. 20 g × 10 μL/g = 200 μL
$^b$B.I.W. stands for dosing frequency of twice a week
$^c$I.T = intratumoral injection. Total volume is split to 3 different injection sites.
$^d$PTS 100 has a concentration of 330 mg/ml. For example, when the dosage is at 330 mg/kg, the volume is 20 g (mice BW) × 1 μL/g = 20 μL
$^e$QW stands for dosing frequency of once a week
$^f$when administering in combination, pemetrexed + cisplatin and PTS are given at different days.

Treatment with PTS as a single agent induced a slight decrease in tumor volume compared to control, while addition of pemetrexed+cisplatin to PTS resulted in a strong decrease in tumor burden, as shown in FIG. 14A. Importantly, the addition of pemetrexed+Cisplatin to PTS greatly enhanced the antitumor activity of PTS in this model with a tumor inhibition of 89.31%.

This effect was most prominent in the group 4 receiving the combination (pemetrexed+cisplatin and PTS) (FIG.

G+C+P that were able to increase the efficacy of the therapeutic effect for lung squamous lung adenocarcinoma.

The above-described descriptions of the detailed embodiments are to illustrate the preferred implementation according to the present disclosure, and it is not to limit the scope of the present disclosure. Accordingly, all modifications and variations completed by those with ordinary skill in the art should fall within the scope of the present disclosure defined by the appended claims.

What is claimed is:

1. A method of treating cancer, comprising administering a therapeutically effective amount of a pharmaceutical composition and a chemotherapy agent to a subject in need thereof, wherein the pharmaceutical composition comprises a benzenesulfonamide derivative and a pharmaceutically acceptable carrier thereof, and the chemotherapy agent comprises pemetrexed and cisplatin, and wherein the pemetrexed is administered to the subject at a dosage of about 100 mg/kg, and the cisplatin is administered to the subject at a dosage of about 2 mg/kg.

2. The method of claim 1, wherein the benzenesulfonamide derivative is represented by formula (I) below:

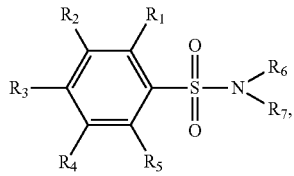

or a pharmaceutically acceptable salt thereof, wherein $R_1$ to $R_7$ are independently selected from the group consisting of H, an optionally substituted $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and wherein the alkyl, alkoxy, cycloalkyl, cycloheteroalkyl groups in $R_1$ to $R_7$ and the ring formed by linking $R_6$ and R_7 is independently unsubstituted or substituted with one or more substituents.

3. The method of claim 2, wherein the one or more substituents are selected from the group consisting of phenyl, halo, oxo, ether, hydroxyl, carboxyl, amino, sulfo and sulfonamide group.

4. The method of claim 3, wherein the benezesulfonamide derivative or the pharmaceutically acceptable salt thereof is at least one compound selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide,

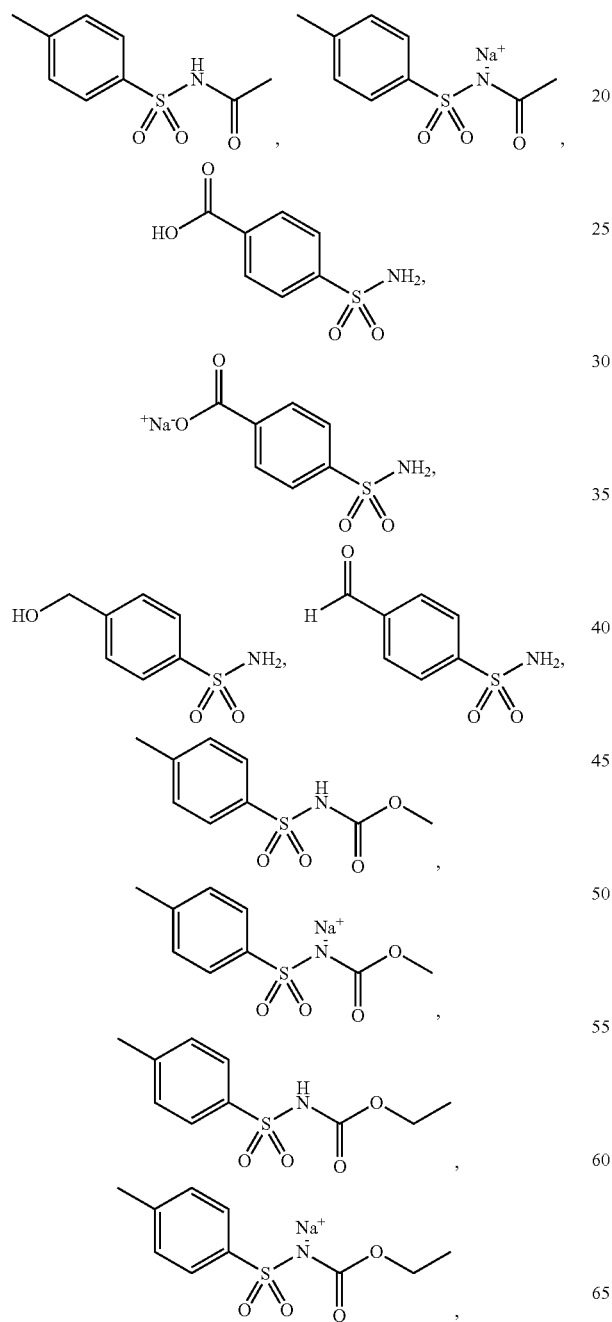

-continued

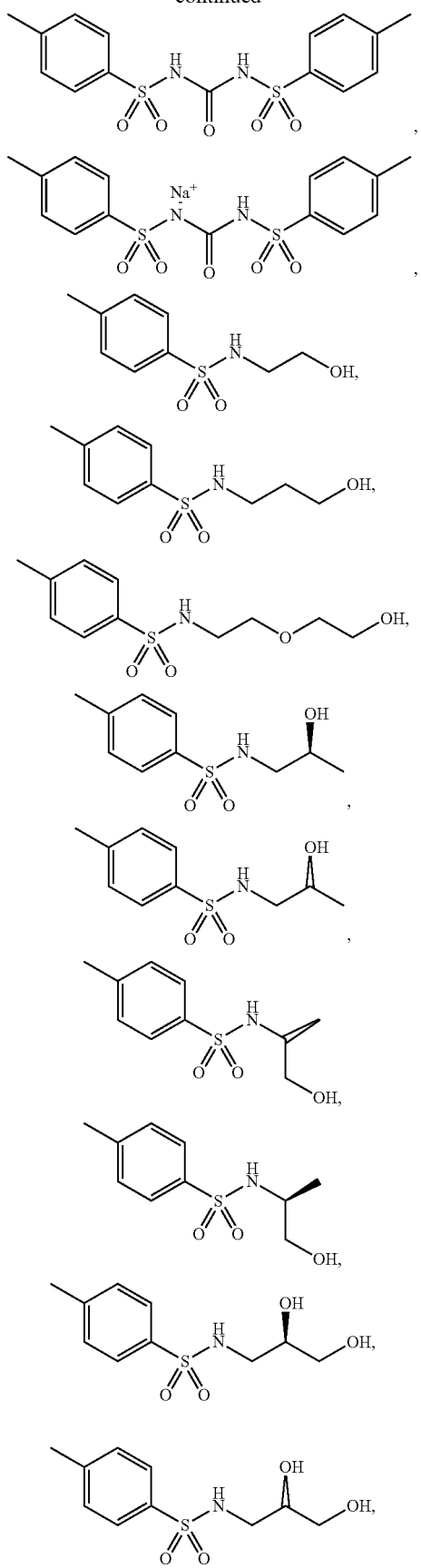

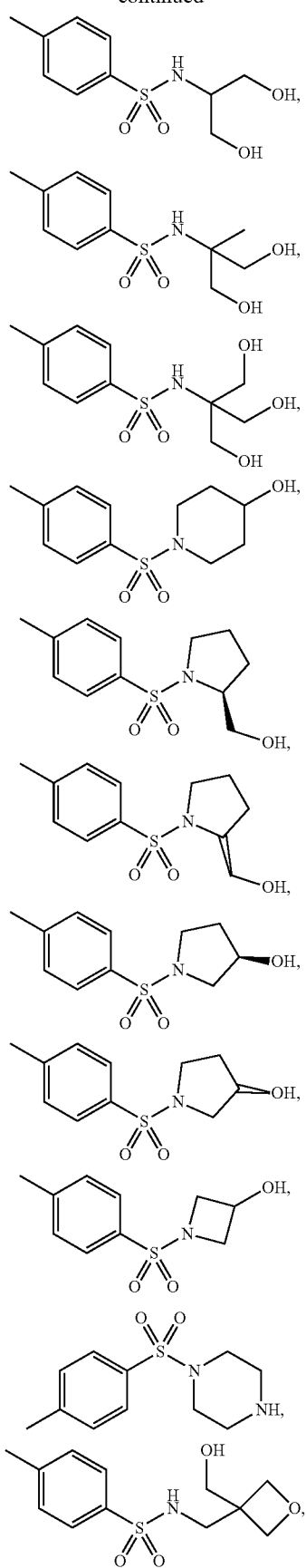
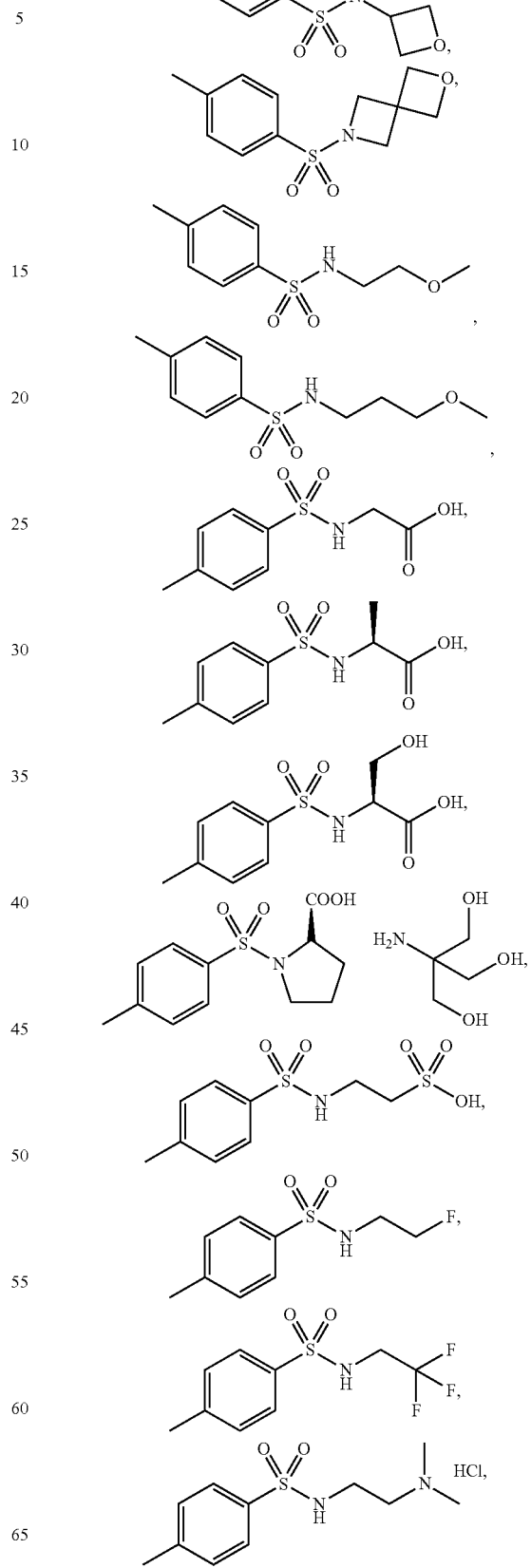

-continued

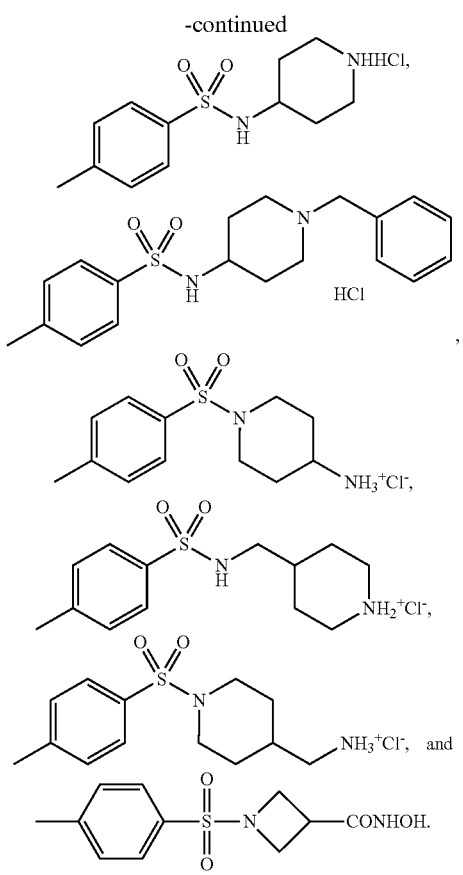

5. The method of claim 1, wherein the cancer is melanoma or lung cancer.

6. The method of claim 5, wherein the cancer is melanoma.

7. The method of claim 6, wherein a ratio of the benzenesulfonamide derivative to the cisplatin is in a range of 25:1 to 2000:1.

8. The method of claim 7, wherein the benzenesulfonamide derivative is administered to the subject at a dosage of about 100 mg/kg.

9. The method of claim 5, wherein the cancer is lung adenocarcinoma.

10. The method of claim 9, wherein a ratio of the benzenesulfonamide derivative to the pemetrexed is in a range of 1.5:1 to 100:1, and a ratio of the benzenesulfonamide derivative to the cisplatin is in a range of 25:1 to 2000:1.

11. The method of claim 10, wherein the benzenesulfonamide derivative is administered to the subject at a dosage of about 330 mg/kg.

12. The method of claim 1, wherein the benzenesulfonamide derivative in the pharmaceutical composition is administered to the subject in an effective amount of from about 3,300 mg to about 26,400 mg.

13. The method of claim 1, wherein the benzenesulfonamide derivative in the pharmaceutical composition is administered to the subject in an effective amount of from about 165 mg to about 6,600 mg per day.

14. The method of claim 1, wherein the pharmaceutical composition or the chemotherapy agent is administered to the subject one time to three times a week.

15. The method of claim 14, wherein the pharmaceutical composition is administered to the subject two times a week, and the chemotherapy agent is administered to the subject one time a week.

16. The method of claim 1, wherein the pharmaceutically acceptable carrier is selected from the group consisting of a filler, a binder, a preservative, a disintegrating agent, a lubricant, a suspending agent, a wetting agent, a flavoring agent, a thickening agent, an acid, a biocompatible solvent, a surfactant, a complexation agent, and any combination thereof.

17. The method of claim 1, wherein the pharmaceutically acceptable carrier is selected from the group consisting of polyethylene glycol, alkylene glycol, propylene glycol, sebacic acid, dimethyl sulfoxide, ethanol, and any combination thereof.

18. The method of claim 1, wherein the pharmaceutical composition is in a form selected from the group consisting of a formulation for injection, dry powder, a tablet, an oral liquid, a wafer, a film, a lozenge, a capsule, a granule, a pill, a gel, a lotion, an ointment, an emulsifier, a paste, a cream, an eye drop, and a salve.

19. The method of claim 1, wherein the pharmaceutical composition or the chemotherapy agent is administered to the subject intratumorally, intravenously, subcutaneously, intradermally, orally, intrathecally, intraperitoneally, intranasally, intramuscularly, intrapleuraly, topically, or through nebulization.

20. The method of claim 1, wherein the subject is a human.

21. The method of claim 1, wherein the subject is a dog, a cat, or a mouse.

* * * * *